(12) United States Patent
Mohr et al.

(10) Patent No.: US 7,534,788 B2
(45) Date of Patent: May 19, 2009

(54) BENZOFURAN AND BENZOTHIOPHENE-2-CARBOXYLIC ACID AMIDE DERIVATIVES

(75) Inventors: Peter Mohr, Basel (CH); Matthias Nettekoven, Grenzach-Wyhlen (DE); Jean-Marc Plancher, Hagenthal-le-Bas (FR); Hans Richter, Grenzach-Whylen (DE); Olivier Roche, Folgensbourg (FR); Tadakatsu Takahashi, Shizuoka (JP); Sven Taylor, Riedisheim (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/173,888

(22) Filed: Jul. 16, 2008

(65) Prior Publication Data

US 2009/0029976 A1    Jan. 29, 2009

(30) Foreign Application Priority Data

Jul. 25, 2007    (EP)    .................................. 07113080

(51) Int. Cl.
    A61K 31/541     (2006.01)
    A61K 31/5377    (2006.01)
    A61K 31/496     (2006.01)
    A61K 31/4545    (2006.01)
    C07D 405/06     (2006.01)
    C07D 409/06     (2006.01)

(52) U.S. Cl. ............ 514/228.2; 514/233.5; 514/253.11; 514/316; 544/58.2; 544/62; 544/121; 544/364; 546/187

(58) Field of Classification Search .................. None
See application file for complete search history.

(56) References Cited

U.S. PATENT DOCUMENTS

| | | |
|---|---|---|
| 4,983,746 A | 1/1991 | Barbier et al. |
| 5,175,186 A | 12/1992 | Barbier et al. |
| 5,245,056 A | 9/1993 | Karpf et al. |
| 5,246,960 A | 9/1993 | Barbier et al. |
| 5,274,143 A | 12/1993 | Ramig et al. |
| 5,399,720 A | 3/1995 | Karpf et al. |
| 5,420,305 A | 5/1995 | Ramig et al. |
| 2008/0188484 A1* | 8/2008 | Nettekoven et al. .... 514/253.01 |

FOREIGN PATENT DOCUMENTS

| | | |
|---|---|---|
| EP | 185 359 | 6/1986 |
| EP | 189 577 | 8/1989 |
| EP | 443 449 | 8/1991 |
| EP | 524 495 | 1/1993 |
| WO | WO 99/34786 | 7/1999 |
| WO | WO 00/09122 | 2/2000 |
| WO | WO 00/09123 | 2/2000 |
| WO | WO 00/58293 | 10/2000 |
| WO | WO 2004/022061 | 3/2004 |
| WO | WO 2004/072051 | 8/2004 |
| WO | WO 2006/035308 | 4/2006 |
| WO | WO 2006/077024 | 7/2006 |
| WO | WO 2007/062997 | 6/2007 |

OTHER PUBLICATIONS

Bridges et al., Tetrahedron Letters, 33, pp. 7499-7502 (1992).
Gallagher et al., Tetrahedron Letters, 41, pp. 5415-5418 (2000).
Bridges et al., Bioorganic & Medicinal Chemistry, 1, pp. 403-410 (1993).

* cited by examiner

*Primary Examiner*—Emily Bernhardt
(74) *Attorney, Agent, or Firm*—George W. Johnston; Patricia S. Rocha-Tramaloni

(57) ABSTRACT

The present invention relates to compounds of formula I

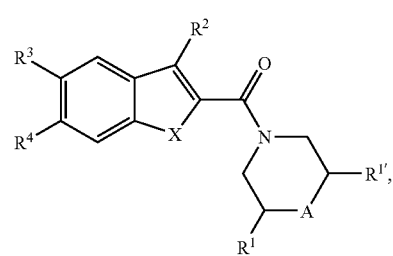

wherein X, A and $R^1$ to $R^4$ are as defined in the description and claims, and pharmaceutically acceptable salts thereof. The compounds are useful for the treatment and/or prevention of diseases which are associated with the modulation of H3 receptors.

20 Claims, No Drawings

BENZOFURAN AND BENZOTHIOPHENE-2-CARBOXYLIC ACID AMIDE DERIVATIVES

PRIORITY TO RELATED APPLICATION(S)

This application claims the benefit of European Patent Application No. 07113080.1 filed Jul. 25, 2007, which is hereby incorporated by reference in its entirety.

SUMMARY OF THE INVENTION

The present invention relates to novel benzofuran- and benzo[b]thiophene-2-carboxylic acid amide derivatives of the formula

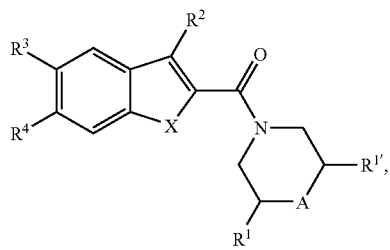

wherein X, A and $R^1$ to $R^4$ are as defined herein and the pharmaceutically acceptable salts thereof along with their manufacture, pharmaceutical compositions containing them and their use as medicaments. The active compounds of the present invention are useful in treating obesity and other disorders.

BACKGROUND OF THE INVENTION

The compounds of formula I are antagonists and/or inverse agonists at the histamine 3 receptor (H3 receptor).

Histamine (2-(4-imidazolyl)ethylamine) is one of the aminergic neurotransmitters which is widely distributed throughout the body, e.g. the gastrointestinal tract (Burks 1994 in Johnson L. R. ed., Physiology of the Gastrointestinal Tract, Raven Press, NY, pp. 211-242). Histamine regulates a variety of digestive pathophysiological events like gastric acid secretion, intestinal motility (Leurs et al., Br. J. Pharmacol. 1991, 102, pp 179-185), vasomotor responses, intestinal inflammatory responses and allergic reactions (Raithel et al., Int. Arch. Allergy Immunol. 1995, 108, 127-133). In the mammalian brain, histamine is synthesized in histaminergic cell bodies which are found centrally in the tubero-mammillary nucleus of the posterior basal hypothalamus. From there, the histaminergic cell bodies project to various brain regions (Panula et al., Proc. Natl. Acad. Sci. USA 1984, 81, 2572-2576; Inagaki et al., J. Comp. Neurol 1988, 273, 283-300).

According to current knowledge, histamine mediates all its actions in both the CNS and the periphery through four distinct histamine receptors, the histamine H1, H2 H3 and H4 receptors, respectively.

H3 receptors are predominantly localized in the central nervous system (CNS). As an autoreceptor H3 receptors constitutively inhibit the synthesis and secretion of histamine from histaminergic neurons (Arrang et al., Nature 1983, 302, 832-837; Arrang et al., Neuroscience 1987, 23, 149-157). As heteroreceptors, H3 receptors also modulate the release of other neurotransmitters such as acetylcholine, dopamine, serotonin and norepinephrine among others in both the central nervous system and in peripheral organs, such as lungs, cardiovascular system and gastrointestinal tract (Clapham & Kilpatrik, Br. J. Pharmacol. 1982, 107, 919-923; Blandina et al., in The Histamine H3 Receptor (Leurs R L and Timmermann H eds, 1998, pp 27-40, Elsevier, Amsterdam, The Netherlands). H3 receptors are constitutively active, meaning that even without exogenous histamine, the receptor is tonically activated. In the case of an inhibitory receptor such as the H3 receptor, this inherent activity causes tonic inhibition of neurotransmitter release. Therefore it may be important that a H3R antagonist would also have inverse agonist activity to both block exogenous histamine effects and to shift the receptor from its constitutively active (inhibitory) form to a neutral state.

The wide distribution of H3 receptors in the mammalian CNS indicates the physiological role of this receptor. Therefore the therapeutic potential as a novel drug development target in various indications has been proposed.

The administration of H3R ligands—as antagonists, inverse agonists, agonists or partial agonists—may influence the histamine levels or the secretion of neurotransmitters in the brain and the periphery and thus may be useful in the treatment of several disorders. Such disorders include obesity (Masaki et al; Endocrinol. 2003, 144, 2741-2748; Hancock et al., European J. of Pharmacol. 2004, 487, 183-197), cardiovascular disorders such as acute myocardial infarction, dementia and cognitive disorders such as attention deficit hyperactivity disorder (ADHD) and Alzheimer's disease, neurological disorders such as schizophrenia, depression, epilepsy, Parkinson's disease, and seizures or convulsions, sleep disorders, narcolepsy, pain, gastrointestinal disorders, vestibular dysfunction such as Morbus Meniere, drug abuse and motion sickness (Timmermann, J. Med. Chem. 1990, 33, 4-11).

It is therefore an object of the present invention to provide selective, directly acting H3 receptor antagonists, respectively inverse agonists. Such antagonists/inverse agonists are useful as therapeutically active substances, particularly in the treatment and/or prevention of diseases which are associated with the modulation of H3 receptors.

DETAILED DESCRIPTION OF THE INVENTION

In particular, the present invention relates to compounds of the general formula

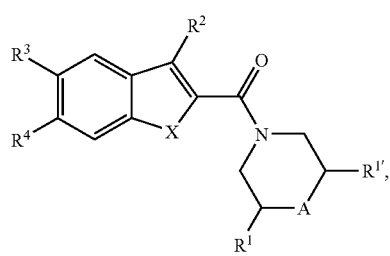

wherein
X is S or O;
A is selected from the group consisting of O, $CF_2$, $S(O)_2$, N—$R^5$ wherein $R^5$ is lower alkyl, NCO—$R^6$ wherein $R^6$ is lower alkyl and NCOO—$R^7$ wherein $R^7$ is lower alkyl;

$R^1$ and $R^{1'}$ independently from each other are hydrogen or lower alkyl;

$R^2$ is selected from the group consisting of hydrogen,
  lower alkyl, cycloalkyl, lower cycloalkylalkyl,
  lower hydroxyalkyl, lower alkoxyalkyl,
  phenyl unsubstituted or substituted with one to three groups independently selected from lower alkyl, halogen, cyano, morpholinyl, lower alkoxy, lower alkoxycarbonyl, lower halogenalkyl, lower halogenalkoxy, lower hydroxyalkyl, lower alkylsulfonyl or lower alkylsulfonylamino,
  lower phenylalkyl, wherein the phenyl ring may be unsubstituted or substituted with one to three groups independently selected from lower alkyl, halogen, cyano, morpholinyl, lower alkoxy, lower alkoxycarbonyl, lower halogenalkyl, lower halogenalkoxy, lower hydroxyalkyl, lower alkylsulfonyl or lower alkylsulfonylamino, and
  heteroaryl unsubstituted or substituted with one or two groups independently selected from lower alkyl, lower alkoxy, cyano, morpholinyl or halogen;

one of $R^3$ or $R^4$ is selected from the group consisting of hydrogen, halogen, lower alkoxy and lower alkyl; and the other one of $R^3$ and $R^4$ is a group G selected from

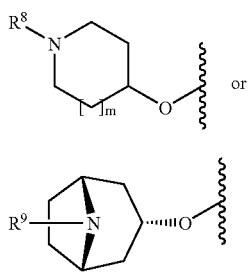

wherein m is 0 or 1;

$R^8$ is selected from the group consisting of lower alkyl, cycloalkyl, lower halogenalkyl and lower alkoxycarbonyl;

$R^9$ is selected from the group consisting of lower alkyl, cycloalkyl, lower halogenalkyl and lower alkoxycarbonyl;

or a pharmaceutically acceptable salt thereof.

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_1$-$C_7$-alkyl", alone or in combination, signifies a straight-chain or branched-chain alkyl group with 1 to 7 carbon atoms, preferably a straight or branched-chain alkyl group with 1 to 6 carbon atoms and particularly preferred a straight or branched-chain alkyl group with 1 to 4 carbon atoms. Examples of straight-chain and branched $C_1$-$C_7$ alkyl groups are methyl, ethyl, propyl, isopropyl, butyl, isobutyl, tert.-butyl, the isomeric pentyls, the isomeric hexyls and the isomeric heptyls, preferably methyl and ethyl and most preferred methyl.

The term "cycloalkyl" or "$C_3$-$C_7$-cycloalkyl" denotes a saturated carbocyclic group containing from 3 to 7 carbon atoms, such as cyclopropyl, cyclobutyl, cyclopentyl, cyclohexyl or cycloheptyl. Especially preferred are cyclobutyl and cyclopentyl.

The term "lower cycloalkylalkyl" or "$C_3$-$C_7$-cycloalkyl-$C_1$-$C_7$-alkyl" refers to lower alkyl groups as defined above wherein at least one of the hydrogen atoms of the lower alkyl group is replaced by cycloalkyl. A preferred example is cyclopropylmethyl.

The term "lower alkoxy" or "$C_1$-$C_7$-alkoxy" refers to the group R'—O—, wherein R' is lower alkyl and the term "lower alkyl" has the previously given significance. Examples of lower alkoxy groups are e.g. methoxy, ethoxy, n-propoxy, isopropoxy, n-butoxy, isobutoxy, sec.-butoxy and tert.-butoxy, preferably methoxy and ethoxy and most preferred ethoxy.

The term "lower hydroxyalkyl" or "hydroxy-$C_1$-$C_7$-alkyl" refers to lower alkyl groups as defined above wherein at least one of the hydrogen atoms of the lower alkyl group is replaced by a hydroxy group. Examples of lower hydroxyalkyl groups are hydroxymethyl or hydroxyethyl. The term "lower alkoxyalkyl" or "$C_1$-$C_7$-alkoxy-$C_1$-$C_7$-alkyl" refers to lower alkyl groups as defined above wherein at least one of the hydrogen atoms of the lower alkyl groups is replaced by an alkoxy group, preferably methoxy or ethoxy. Among the preferred lower alkoxyalkyl groups are 2-methoxyethyl or 3-methoxypropyl.

The term "halogen" refers to fluorine, chlorine, bromine and iodine, with fluorine, chlorine and bromine being preferred.

The term "lower halogenalkyl" or "halogen-$C_1$-$C_7$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, trifluoroethyl, 2,2-difluoroethyl, fluoromethyl and chloromethyl, with trifluoromethyl or 2,2-difluoroethyl being especially preferred.

The term "lower halogenalkoxy" or "halogen-$C_1$-$C_7$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkoxy groups are trifluoromethoxy, difluoromethoxy, fluormethoxy and chloromethoxy, with trifluoromethoxy being especially preferred.

The term "alkylsulfonyl" or "lower alkylsulfonyl" refers to the group R'—S(O)$_2$—, wherein R' is lower alkyl and the term "lower alkyl" has the previously given significance. Examples of alkylsulfonyl groups are e.g. methylsulfonyl or ethylsulfonyl.

The term "alkylsulfonylamino" or "lower alkylsulfonylamino" refers to the group R'—S(O)$_2$—NH—, wherein R' is lower alkyl and the term "lower alkyl" has the previously given significance. Examples of alkylsulfonylamino groups are e.g. methylsulfonylamino or ethylsulfonylamino.

The term "lower alkoxycarbonyl" or "$C_1$-$C_7$-alkoxycarbonyl" refers to the group —CO—OR' wherein R' is lower alkyl and the term "lower alkyl" has the previously given significance. Preferred lower alkoxycarbonyl groups are methoxycarbonyl or ethoxycarbonyl. The term "lower phenylalkyl" or "phenyl-$C_1$-$C_7$-alkyl" refers to lower alkyl groups as defined above wherein at least one of the hydrogen atoms of the lower alkyl group is replaced by a phenyl group. The phenyl group may be further substituted. Preferred lower phenylalkyl groups are benzyl or phenethyl.

The term "heteroaryl" in general refers to an aromatic 5- or 6-membered ring which can comprise one, two or three atoms selected from nitrogen, oxygen and/or sulphur such as furyl, pyridyl, 1,2-, 1,3- and 1,4-diazinyl, thienyl, isoxazolyl, oxazolyl, imidazolyl, or pyrrolyl. The term "heteroaryl" further refers to bicyclic aromatic groups comprising two 5- or 6-membered rings, in which one or both rings can contain one, two or three atoms selected from nitrogen, oxygen or sulphur, such as e.g. indole or quinoline. A preferred heteroaryl group is pyridyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compounds of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I or II (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers.

The present invention is concerned with compounds of the general formula

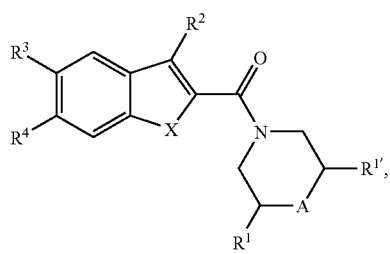

I wherein

X is S or O;

A is selected from the group consisting of O, $CF_2$, $S(O)_2$, $N-R^5$ wherein $R^5$ is lower alkyl, $NCO-R^6$ wherein $R^6$ is lower alkyl and $NCOO-R^7$ wherein $R^7$ is lower alkyl;

$R^1$ and $R^{1'}$ independently from each other are hydrogen or lower alkyl;

$R^2$ is selected from the group consisting of hydrogen,
  lower alkyl, cycloalkyl, lower cycloalkylalkyl,
  lower hydroxyalkyl, lower alkoxyalkyl,
  phenyl unsubstituted or substituted with one to three groups independently selected from lower alkyl, halogen, cyano, morpholinyl, lower alkoxy, lower alkoxycarbonyl, lower halogenalkyl, lower halogenalkoxy, lower hydroxyalkyl, lower alkylsulfonyl and lower alkylsulfonylamino,
  lower phenylalkyl, wherein the phenyl ring may be unsubstituted or substituted with one to three groups independently selected from lower alkyl, halogen, cyano, morpholinyl, lower alkoxy, lower alkoxycarbonyl, lower halogenalkyl, lower halogenalkoxy, lower hydroxyalkyl, lower alkylsulfonyl and lower alkylsulfonylamino, and
  heteroaryl unsubstituted or substituted with one or two groups independently selected from lower alkyl, lower alkoxy, cyano, morpholinyl and halogen;

one of $R^3$ or $R^4$ is selected from the group consisting of hydrogen, halogen, lower alkoxy and lower alkyl; and the other one of $R^3$ and $R^4$ is a group G selected from

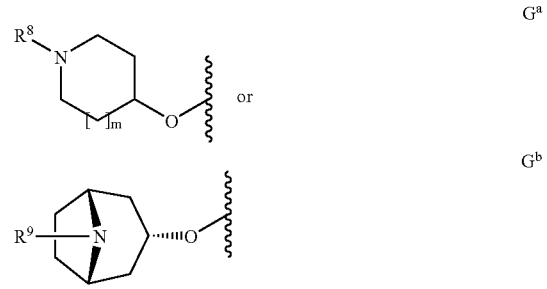

wherein m is 0 or 1;

$R^8$ is selected from the group consisting of lower alkyl, cycloalkyl, lower halogenalkyl and lower alkoxycarbonyl;

$R^9$ is selected from the group consisting of lower alkyl, cycloalkyl, lower halogenalkyl and lower alkoxycarbonyl;

and pharmaceutically acceptable salts thereof.

A preferred group of compounds of formula I according to the present invention are those, wherein X is O.

Compounds of formula I, wherein X is S, are also preferred.

Preferred are further compounds of formula I according to the present invention, wherein A is $S(O)_2$, meaning compounds of formula I having the formula

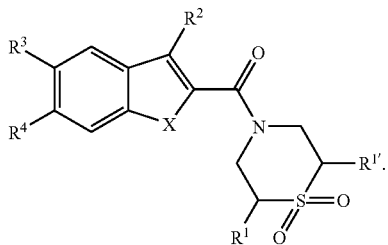

Ia wherein X, $R^1$, $R^{1'}$, $R^2$, $R^3$ and $R^4$ are as defined herein before, and pharmaceutically acceptable salts thereof.

In addition, compounds of formula I according to the invention are preferred, wherein A is selected from the group consisting of N—$R^5$ wherein $R^5$ is lower alkyl, NCO—$R^6$ wherein $R^6$ is lower alkyl, and NCOO—$R^7$ wherein $R^7$ is lower alkyl.

Preferably, $R^5$ is isopropyl. Preferred $R^6$ is methyl.

More preferred are compounds of formula I, wherein A is NCOO—$R^7$ wherein $R^7$ is lower alkyl, meaning compounds of formula I having the formula

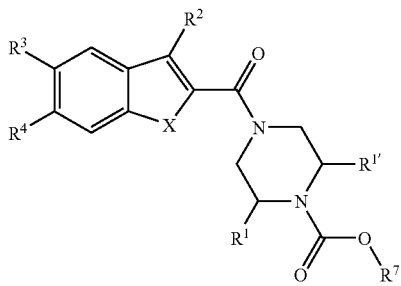

Ib wherein X, $R^1$, $R^{1'}$, $R^2$, $R^3$ and $R^4$ are as defined herein before, and pharmaceutically acceptable salts thereof.

Most preferably, $R^7$ is methyl or tert-butyl.

Also preferred are compounds of formula I according to the present invention, wherein A is $CF_2$, meaning compounds of formula I having the formula

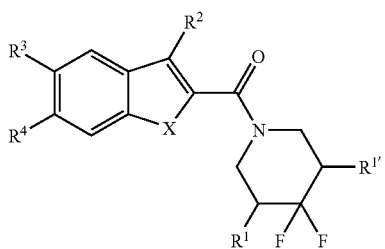

Ic wherein X, $R^1$, $R^{1'}$, $R^2$, $R^3$ and $R^4$ are as defined herein before, and pharmaceutically acceptable salts thereof.

Preferred are furthermore compounds of formula Ic according to the present invention, wherein $R^1$ and $R^{1'}$ are independently selected from hydrogen or methyl. More preferred are those compounds of formula Ic, wherein $R^1$ and $R^{1'}$ are hydrogen.

In addition, compounds of formula I according to the present invention are preferred, wherein A is O, meaning compounds of formula I having the formula

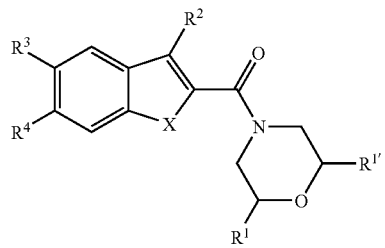

Id wherein X, $R^1$, $R^{1'}$, $R^2$, $R^3$ and $R^4$ are as defined herein before, and pharmaceutically acceptable salts thereof.

Especially preferred are compounds of formula Id, wherein $R^1$ and $R^{1'}$ are methyl.

Furthermore, compounds of formula I according to the present invention are preferred, wherein $R^2$ is selected from the group consisting of hydrogen, lower alkyl, and phenyl unsubstituted or substituted with one to three groups independently selected from lower alkyl, halogen, cyano, morpholinyl, lower alkoxy, lower alkoxycarbonyl, lower halogenalkyl, lower halogenalkoxy, lower hydroxyalkyl, lower alkylsulfonyl and lower alkylsulfonylamino, with those compounds being more preferred, wherein $R^2$ is unsubstituted phenyl or phenyl substituted with one to three halogen groups, most preferably $R^2$ is phenyl or 4-fluorophenyl.

Compounds of formula I according to the invention are also preferred, wherein one of $R^3$ or $R^4$ is selected from the group consisting of hydrogen, halogen and lower alkyl; and the other one of $R^3$ and $R^4$ is a group G selected from

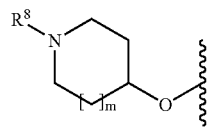

$G^a$

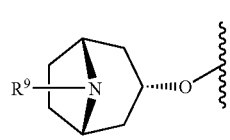

$G^b$ wherein m is 0 or 1;

$R^8$ is selected from the group consisting of lower alkyl, cycloalkyl, lower halogenalkyl and lower alkoxycarbonyl;

$R^9$ is selected from the group consisting of lower alkyl, cycloalkyl, lower halogenalkyl and lower alkoxycarbonyl.

Especially preferred are compounds of formula I according to the present invention, wherein one of $R^3$ or $R^4$ is selected from the group consisting of hydrogen, halogen and lower alkyl; and the other one of $R^3$ and $R^4$ is the group $G^a$

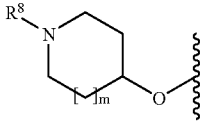

wherein m is 0 or 1; and $R^8$ is selected from the group consisting of lower alkyl, cycloalkyl, lower halogenalkyl and lower alkoxycarbonyl.

More preferred are compounds of formula I according to the present invention, wherein one of $R^3$ or $R^4$ is hydrogen and the other one of $R^3$ and $R^4$ is

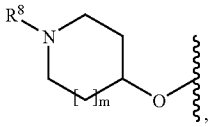

wherein m is 0 or 1; and $R^8$ is selected from the group consisting of lower alkyl, cycloalkyl, lower halogenalkyl and lower alkoxycarbonyl.

Preferred are compounds of formula I, wherein $R^8$ is lower alkyl or cycloalkyl, especially preferred are those compounds, wherein $R^8$ is isopropyl or cyclobutyl.

Preferred are further compounds of formula I according to the invention, wherein m is 1.

Preferred compounds of formula I of the present invention are the following:

(1,1-dioxo-$_1\lambda$6-thiomorpholin-4-yl)-[5-(1-isopropyl-piperidin-4-yloxy)-benzofuran-2-yl]-methanone,
(cis-2,6-dimethyl-morpholin-4-yl)-[5-(1-isopropyl-piperidin-4-yloxy)-benzofuran-2-yl]-methanone,
(4-isopropyl-piperazin-1-yl)-[5-(1-isopropyl-piperidin-4-yloxy)-benzofuran-2-yl]-methanone,
(4,4-difluoro-piperidin-1-yl)-[5-(1-isopropyl-piperidin-4-yloxy)-benzofuran-2-yl]-methanone,
4-[5-(1-isopropyl-piperidin-4-yloxy)-benzofuran-2-carbonyl]-piperazine-1-carboxylic acid tert-butyl ester,
(4,4-difluoro-piperidin-1-yl)-[5-(1-isopropyl-piperidin-4-yloxy)-benzo[b]thiophen-2-yl]-methanone,
(4,4-difluoro-piperidin-1-yl)-[6-(1-isopropyl-piperidin-4-yloxy)benzo[b]thiophen-2-yl]-methanone,
(4,4-difluoro-piperidin-1-yl)-[3-isopropyl-6-(1-isopropyl-piperidin-4-yloxy)-benzofuran-2-yl]-methanone,
4-[5-(1-isopropyl-piperidin-4-yloxy)-benzo[b]thiophene-2-carbonyl]-piperazine-1-carboxylic acid tert-butyl ester,
(1,1-dioxo-$_1\lambda$6-thiomorpholin-4-yl)-[5-(1-isopropyl-piperidin-4-yloxy)-benzo[b]thiophen-2-yl]-methanone,
(1,1-dioxo-$_1\lambda$6thiomorpholin-4-yl)-[5-(1-isopropyl-piperidin-4-yloxy)-6-methyl-benzofuran-2-yl]-methanone,
((cis)-2,6-dimethyl-morpholin-4-yl)-[5-(1-isopropyl-piperidin-4-yloxy)-6-methyl-benzofuran-2-yl]-methanone,
(4,4-difluoro-piperidin-1-yl)-[5-(1-isopropyl-piperidin-4-yloxy)-6-methyl-benzofuran-2-yl]-methanone,
1-{4-[5-(1-isopropyl-piperidin-4-yloxy)-6-methyl-benzofuran-2-carbonyl]-piperazin-1-yl}-ethanone,
4-[5-(1-isopropyl-piperidin-4-yloxy)-6-methyl-benzofuran-2-carbonyl]-piperazine-1-carboxylic acid methyl ester,
(4,4-difluoro-piperidin-1-yl)-[6-(1-isopropyl-piperidin-4-yloxy)-benzofuran-2-yl]-methanone,
(4,4-difluoro-piperidin-1-yl)-[6-(1-isopropyl-piperidin-4-yloxy)-3-phenyl-benzofuran-2-yl]-methanone,
4-[6-(1-isopropyl-piperidin-4-yloxy)-benzofuran-2-carbonyl]-piperazine-1-carboxylic acid methyl ester,
[6-(1-cyclobutyl-piperidin-4-yloxy)-benzo[b]thiophen-2-yl]-(4,4-difluoro-piperidin-1-yl)methanone,
[6-(1-cyclobutyl-piperidin-4-yloxy)-benzo[b]thiophen-2-yl]-((cis)-2,6-dimethyl-morpholin-4-yl)-methanone,
[6-(1-cyclobutyl-piperidin-4-yloxy)-benzofuran-2-yl]-(4,4-difluoro-piperidin-1-yl)-methanone,
[6-(1-cyclobutyl-piperidin-4-yloxy)-benzofuran-2-yl]-((cis)-2,6-dimethyl-morpholin-4-yl)-methanone,
[5-(1-cyclobutyl-piperidin-4-yloxy)-6-methyl-benzofuran-2-yl]-(4,4-difluoro-piperidin-1-yl)-methanone,
[5-(1-cyclobutyl-piperidin-4-yloxy)-6-methyl-benzofuran-2-yl]-(1,1-dioxo-$_1\lambda$6thiomorpholin-4-yl)methanone,
[5-(1-cyclobutyl-piperidin-4-yloxy)-6-methyl-benzofuran-2-yl]-((cis)-2,6-dimethyl-morpholin-4-yl)-methanone,
4-[5-(1-cyclobutyl-piperidin-4-yloxy)-6-methyl-benzofuran-2-carbonyl]-piperazine-1-carboxylic acid methyl ester,
[6-(1-cyclobutyl-piperidin-4-yloxy)-benzofuran-2-yl]-(1,1-dioxo-$_1\lambda$6thiomorpholin-4-yl)-methanone,
[6-chloro-5-(1-isopropyl-piperidin-4-yloxy)-benzofuran-2-yl]-(4,4-difluoro-piperidin-1-yl)-methanone,
[6-chloro-5-(1-isopropyl-piperidin-4-yloxy)-benzofuran-2-yl]-((cis)-2,6-dimethyl-morpholin-4-yl)-methanone,
[6-chloro-5-(1-isopropyl-piperidin-4-yloxy)-benzofuran-2-yl]-(1,1-dioxo-1$1%6&-thiomorpholin-4-yl)-methanone,
[5-(1-cyclobutyl-piperidin-4-yloxy)-benzo)[b]thiophen-2-yl]-(4,4-difluoro-piperidin-1-yl)-methanone,
[5-(1-cyclobutyl-piperidin-4-yloxy)-benzo[b]thiophen-2-yl]-((cis)-2,6-dimethyl-morpholin-4-yl)-methanone,
4-[5-(1-isopropyl-piperidin-4-yloxy)-benzo[b]thiophene-2-carbonyl]-piperazine-1-carboxylic acid methyl ester,
4-[6-(1-isopropyl-piperidin-4-yloxy)-3-phenyl-benzofuran-2-carbonyl]-piperazine-1-carboxylic acid methyl ester,
((cis)-2,6-dimethyl-morpholin-4-yl)-[6-(1-isopropyl-piperidin-4-yloxy)-3-phenyl-benzofuran-2-yl]-methanone,
[5-chloro-3-isopropyl-6-(1-isopropyl-piperidin-4-yloxy)-benzofuran-2-yl]-(4,4-difluoro-piperidin-1-yl)-methanone,
((cis)-2,6-dimethyl-morpholin-4-yl)-[6-(1-isopropyl-piperidin-4-yloxy)-5-methyl-3-phenyl-benzofuran-2-yl]-methanone,
4-[6-(1-isopropyl-piperidin-4-yloxy)-5-methyl-3-phenyl-benzofuran-2-carbonyl]-piperazine-1-carboxylic acid methyl ester,
(1,1-dioxo-$_1\lambda$6thiomorpholin-4-yl)-[6-(1-isopropyl-piperidin-4-yloxy)-5-methyl-3-phenyl-benzofuran-2-yl]-methanone,
(4,4-difluoro-piperidin-1-yl)-[6-(1-isopropyl-piperidin-4-yloxy)-5-methyl-3-phenyl-benzofuran-2-yl]-methanone,
[5-(1-cyclobutyl-piperidin-4-yloxy)-benzofuran-2-yl]-((cis)-2,6-dimethyl-morpholin-4-yl)-methanone,
[5-(1-cyclobutyl-piperidin-4-yloxy)-benzofuran-2-yl]-(4,4-difluoro-piperidin-1-yl)-methanone,
[5-(1-cyclobutyl-piperidin-4-yloxy)-benzofuran-2-yl]-(1,1-dioxo-$_1\lambda$6-thiomorpholin-4-yl)-methanone,
4-[5-(1-cyclobutyl-piperidin-4-yloxy)-benzofuran-2-carbonyl]-piperazine-1-carboxylic acid methyl ester,
4-[3-(4-fluoro-phenyl)-6-(1-isopropyl-piperidin-4-yloxy)-benzofuran-2-carbonyl]-piperazine-1-carboxylic acid methyl ester, ((cis)-2,6-dimethyl-morpholin-4-yl)-[3-(4-fluoro-phenyl)-6-(1-isopropyl-piperidin-4-yloxy)-benzofuran-2-yl]-methanone,
(1,1-dioxo-$_1\lambda$6thiomorpholin-4-yl)-[3-(4-fluoro-phenyl)-6-(1- isopropyl- piperidin-4-yloxy)-benzofuran-2-yl]-methanone,
(4,4-difluoro-piperidin-1-yl)-[3-(4-fluoro-phenyl)-6-(1-isopropyl-piperidin-4-yloxy)-benzofuran-2-yl]-methanone,
(4,4-difluoro-piperidin-1-yl)-[3-isopropyl-6-(1-isopropyl-piperidin-4-yloxy)-5-methyl-benzofuran-2-yl]-methanone,
((cis)-2,6-dimethyl-morpholin-4-yl)-[3-isopropyl-6-(1-isopropyl-piperidin-4-yloxy)-5-methyl-benzofuran-2-yl]-methanone,
(1,1-dioxo-$_1\lambda$6thiomorpholin-4-yl)-[3-isopropyl-6-(1-isopropyl- piperidin-4-yloxy)-5-methyl-benzofuran-2-yl]-methanone,
[5-chloro-6-(1-isopropyl-piperidin-4-yloxy)-3-phenyl-benzofuran-2-yl]-(4,4-difluoro-piperidin-1-yl)-methanone,
4-[3-isopropyl-6-(1-isopropyl-piperidin-4-yloxy)-5-methyl-benzofuran-2-carbonyl]-piperazine-1-carboxylic acid methyl ester,
4-[5-chloro-6-(1-isopropyl-piperidin-4-yloxy)-3-phenyl-benzofuran-2-carbonyl]-piperazine-1-carboxylic acid methyl ester,
[6-(1-cyclobutyl-piperidin-4-yloxy)-3-phenyl-benzofuran-2-yl]-(4,4-difluoro-piperidin-1-yl)-methanone,
[6-(1-cyclobutyl-piperidin-4-yloxy)-3-phenyl-benzofuran-2-yl]-(1,1-dioxo-$_1\lambda$6thiomorpholin-4-yl)-methanone,
[6-(1-cyclobutyl-piperidin-4-yloxy)-3-phenyl-benzofuran-2-yl]-((cis)-2,6-dimethyl-morpholin-4-yl)-methanone,
[6-(1-cyclobutyl-piperidin-4-yloxy)-3-isopropyl-5-methyl-benzofuran-2-yl]-(4,4-difluoro-piperidin-1-yl)-methanone,
[6-(1-cyclobutyl-piperidin-4-yloxy)-3-isopropyl-5-methyl-benzofuran-2-yl]-((cis)-2,6-dimethyl-morpholin-4-yl)-methanone,
[6-(1-cyclobutyl-piperidin-4-yloxy)-3-isopropyl-5-methyl-benzofuran-2-yl]-(1,1-dioxo-$_1\lambda$6thiomorpholin-4-yl)-methanone,
4-[6-(1-cyclobutyl-piperidin-4-yloxy)-3-isopropyl-5-methyl-benzofuran-2-carbonyl]-piperazine-1-carboxylic acid methyl ester,
4-[6-(1-cyclobutyl-piperidin-4-yloxy)-3-phenyl-benzofuran-2-carbonyl]-piperazine-1-carboxylic acid methyl ester,
4-[6-(1-cyclobutyl-piperidin-4-yloxy)-3-(4-fluoro-phenyl)-benzofuran-2-carbonyl]-piperazine-1-carboxylic acid methyl ester,
[6-(1-cyclobutyl-piperidin-4-yloxy)-3-(4-fluoro-phenyl)-benzofuran-2-yl]-((cis)-2,6-dimethyl-morpholin-4-yl)-methanone,
[6-(1-cyclobutyl-piperidin-4-yloxy)-3-(4-fluoro-phenyl)-benzofuran-2-yl]-(4,4-difluoro-piperidin-1-yl)-methanone,
(1,1-dioxo-$_1\lambda$6thiomorpholin-4-yl)-[6-(1-isopropyl-piperidin-4-yloxy)-3-phenyl-benzofuran-2-yl]-methanone,
[6-(1-cyclobutyl-piperidin-4-yloxy)-3-(4-fluoro-phenyl)-benzofuran-2-yl]-(1,1-dioxo-$_1\lambda$6thiomorpholin-4-yl)-methanone,
4-[6-chloro-5-(1-isopropyl-piperidin-4-yloxy)-benzo[b]thiophene-2-carbonyl]-piperazine-1-carboxylic acid methyl ester,
[6-chloro-5-(1-isopropyl-piperidin-4-yloxy)-benzo[b]thiophen-2-yl]-(1,1-dioxo-$_1\lambda$6thiomorpholin-4-yl)-methanone,

[5-chloro-3-isopropyl-6-(1-isopropyl-piperidin-4-yloxy)-benzofuran-2-yl]-((cis)-2,6-dimethyl-morpholin-4-yl)-methanone,
[5-chloro-3-isopropyl-6-(1-isopropyl-piperidin-4-yloxy)-benzofuran-2-yl]-(1,1-dioxo-$_1\lambda$6thiomorpholin-4-yl)-methanone,
4-[5-chloro-3-isopropyl-6-(1-isopropyl-piperidin-4-yloxy)-benzofuran-2-carbonyl]-piperazine-1-carboxylic acid methyl ester,
[5-chloro-6-(1-cyclobutyl-piperidin-4-yloxy)-3-isopropyl-benzofuran-2-yl]-(4,4-difluoro-piperidin-1-yl)-methanone,
[5-chloro-6-(1-cyclobutyl-piperidin-4-yloxy)-3-isopropyl-benzofuran-2-yl]-((cis)-2,6-dimethyl-morpholin-4-yl)-methanone,
[5-chloro-6-(1-cyclobutyl-piperidin-4-yloxy)-3-isopropyl-benzofuran-2-yl]-(1,1-dioxo-$_1\lambda$6thiomorpholin-4-yl)-methanone,
4-[5-chloro-6-(1-cyclobutyl-piperidin-4-yloxy)-3-isopropyl-benzofuran-2-carbonyl]-piperazine-1-carboxylic acid methyl ester,
[5-chloro-6-(1-cyclobutyl-piperidin-4-yloxy)-3-phenyl-benzofuran-2-yl]-(1,1-dioxo-$_1\lambda$6thiomorpholin-4-yl)-methanone,
4-[5-chloro-6-(1-cyclobutyl-piperidin-4-yloxy)-3-phenyl-benzofuran-2-carbonyl]-piperazine-1-carboxylic acid methyl ester,
4-[5-chloro-3-(4-fluoro-phenyl)-6-(1-isopropyl-piperidin-4-yloxy)-benzofuran-2-carbonyl]-piperazine-1-carboxylic acid methyl ester,
[5-chloro-3-(4-fluoro-phenyl)-6-(1-isopropyl-piperidin-4-yloxy)-benzofuran-2-yl]-((cis)-2,6-dimethyl-morpholin-4-yl)-methanone,
[5-chloro-3-(4-fluoro-phenyl)-6-(1-isopropyl-piperidin-4-yloxy)-benzofuran-2-yl]-(4,4-difluoro-piperidin-1-yl)-methanone,
[5-chloro-3-(4-fluoro-phenyl)-6-(1-isopropyl-piperidin-4-yloxy)-benzofuran-2-yl]-(1,1-dioxo-$_1\lambda$6thiomorpholin-4-yl)-methanone,
4-[5-chloro-6-(1-cyclobutyl-piperidin-4-yloxy)-3-(4-fluoro-phenyl)-benzofuran-2-carbonyl]-piperazine-1-carboxylic acid methyl ester,
[5-chloro-6-(1-cyclobutyl-piperidin-4-yloxy)-3-(4-fluoro-phenyl)-benzofuran-2-yl]-(cis)-2,6-dimethyl-morpholin-4-yl)-methanone,
[5-chloro-6-(1-cyclobutyl-piperidin-4-yloxy)-3-(4-fluoro-phenyl)-benzofuran-2-yl]-(1,1-dioxo-$_1\lambda$6thiomorpholin-4-yl)-methanone,
[5-chloro-6-(1-cyclobutyl-piperidin-4-yloxy)-3-(4-fluoro-phenyl)-benzofuran-2-yl]-(4,4-difluoro-piperidin-1-yl)-methanone,
[5-chloro-6-(1-isopropyl-piperidin-4-yloxy)-3-methyl-benzofuran-2-yl]-(4,4-difluoro-piperidin-1-yl)-methanone,
[5-chloro-6-(1-isopropyl-piperidin-4-yloxy)-3-methyl-benzofuran-2-yl]-((cis)-2,6-dimethyl-morpholin-4-yl)-methanone,
[5-chloro-6-(1-isopropyl-piperidin-4-yloxy)-3-methyl-benzofuran-2-yl]-(1,1-dioxo-$_1\lambda$6-thiomorpholin-4-yl)-methanone,
4-[5-chloro-6-(1-isopropyl-piperidin-4-yloxy)-3-methyl-benzofuran-2-carbonyl]-piperazine-1-carboxylic acid methyl ester,
[5-chloro-6-(1-cyclobutyl-piperidin-4-yloxy)-3-methyl-benzofuran-2-yl]-(4,4-difluoro-piperidin-1-yl)-methanone,

[5-chloro-6-(1-cyclobutyl-piperidin-4-yloxy)-3-methyl-benzofuran-2-yl]-((cis)-2,6-dimethyl-morpholin-4-yl)-methanone,
[5-chloro-6-(1-cyclobutyl-piperidin-4-yloxy)-3-methyl-benzofuran-2-yl]-(1,1-dioxo-$_1\lambda$6thiomorpholin-4-yl)-methanone,
4-[5-chloro-6-(1-cyclobutyl-piperidin-4-yloxy)-3-methyl-benzofuran-2-carbonyl]-piperazine-1-carboxylic acid methyl ester, and pharmaceutically acceptable salts thereof.

Especially preferred compounds of formula I of the present invention are the following:
[5-(1-cyclobutyl-piperidin-4-yloxy)-benzofuran-2-yl]-(4,4-difluoro-piperidin-1-yl)-methanone,
4-[3-(4-fluoro-phenyl)-6-(1-isopropyl-piperidin-4-yloxy)-benzofuran-2-carbonyl]-piperazine-1-carboxylic acid methyl ester,
4-[6-(1-cyclobutyl-piperidin-4-yloxy)-3-phenyl-benzofuran-2-carbonyl]-piperazine-1-carboxylic acid methyl ester,
4-[6-(1-cyclobutyl-piperidin-4-yloxy)-3-(4-fluoro-phenyl)-benzofuran-2-carbonyl]-piperazine-1-carboxylic acid methyl ester,
[6-(1-cyclobutyl-piperidin-4-yloxy)-3-(4-fluoro-phenyl)-benzofuran-2-yl]-((cis)-2,6-dimethyl-morpholin-4-yl)-methanone,
[6-(1-cyclobutyl-piperidin-4-yloxy)-3-(4-fluoro-phenyl)-benzofuran-2-yl]-(4,4-difluoro-piperidin-1-yl)-methanone,
[6-(1-cyclobutyl-piperidin-4-yloxy)-3-(4-fluoro-phenyl)-benzofuran-2-yl]-(1,1-dioxo-$_1\lambda$6thiomorpholin-4-yl)-methanone,
4-[5-chloro-6-(1-cyclobutyl-piperidin-4-yloxy)-3-phenyl-benzofuran-2-carbonyl]-piperazine-1-carboxylic acid methyl ester,
4-[5-chloro-3-(4-fluoro-phenyl)-6-(1-isopropyl-piperidin-4-yloxy)-benzofuran-2-carbonyl]-piperazine-1-carboxylic acid methyl ester,
[5-chloro-3-(4-fluoro-phenyl)-6-(1-isopropyl-piperidin-4-yloxy)-benzofuran-2-yl]-(1,1-dioxo-$_1\lambda$6thiomorpholin-4-yl)-methanone,
4-[5-chloro-6-(1-cyclobutyl-piperidin-4-yloxy)-3-(4-fluoro-phenyl)-benzofuran-2-carbonyl]-piperazine-1-carboxylic acid methyl ester,
[5-chloro-6-(1-cyclobutyl-piperidin-4-yloxy)-3-(4-fluoro-phenyl)-benzofuran-2-yl]-(1,1-dioxo-$_1\lambda$6thiomorpholin-4-yl)-methanone, and pharmaceutically acceptable salts thereof.

Furthermore, the pharmaceutically acceptable salts of the compounds of formula I constitute preferred embodiments of the present invention.

Compounds of formula I may form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartarate, and methanesulphonate. Preferred are the hydrochloride salts. Also solvates and hydrates of compounds of formula I and their salts form part of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises reacting a compound of the formula II

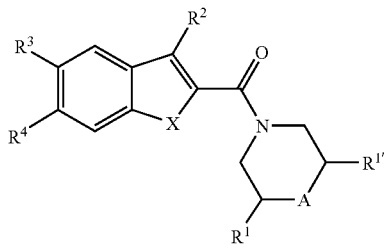

wherein X, A, $R^1$, $R^{1'}$ and $R^2$ are as defined herein before, one of $R^3$ or $R^4$ is selected from the group consisting of hydrogen, halogen and lower alkyl, and the other one of $R^3$ and $R^4$ is hydroxy, with an alcohol of the formula III

G-H    III wherein G is a group $G^a$ or $G^b$ as defined herein before, in the presence of a trialkylphosphine or triphenylphosphine and of an azo compound to obtain a compound of the formula I

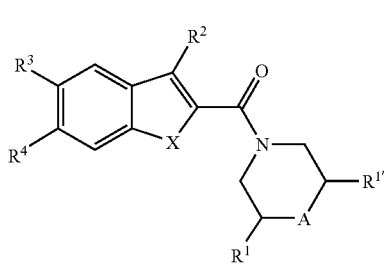

and, if desired, converting the compound obtained into a pharmaceutically acceptable salt.

An azo compound means for example an azodicarboxylic acid dialkyl ester such as, e.g., diethyl azodicarboxylate (DEAD) or diisopropyl azodicarboxylate (DIAD) (optionally polymer bound), di-tert-butyl azodicarboxylate, or N,N,N', N'-tetramethyl azo-dicarboxamide.

In more detail, the compounds of formula I can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

The synthesis of compounds with the general structure I is described in schemes 1 to 9.
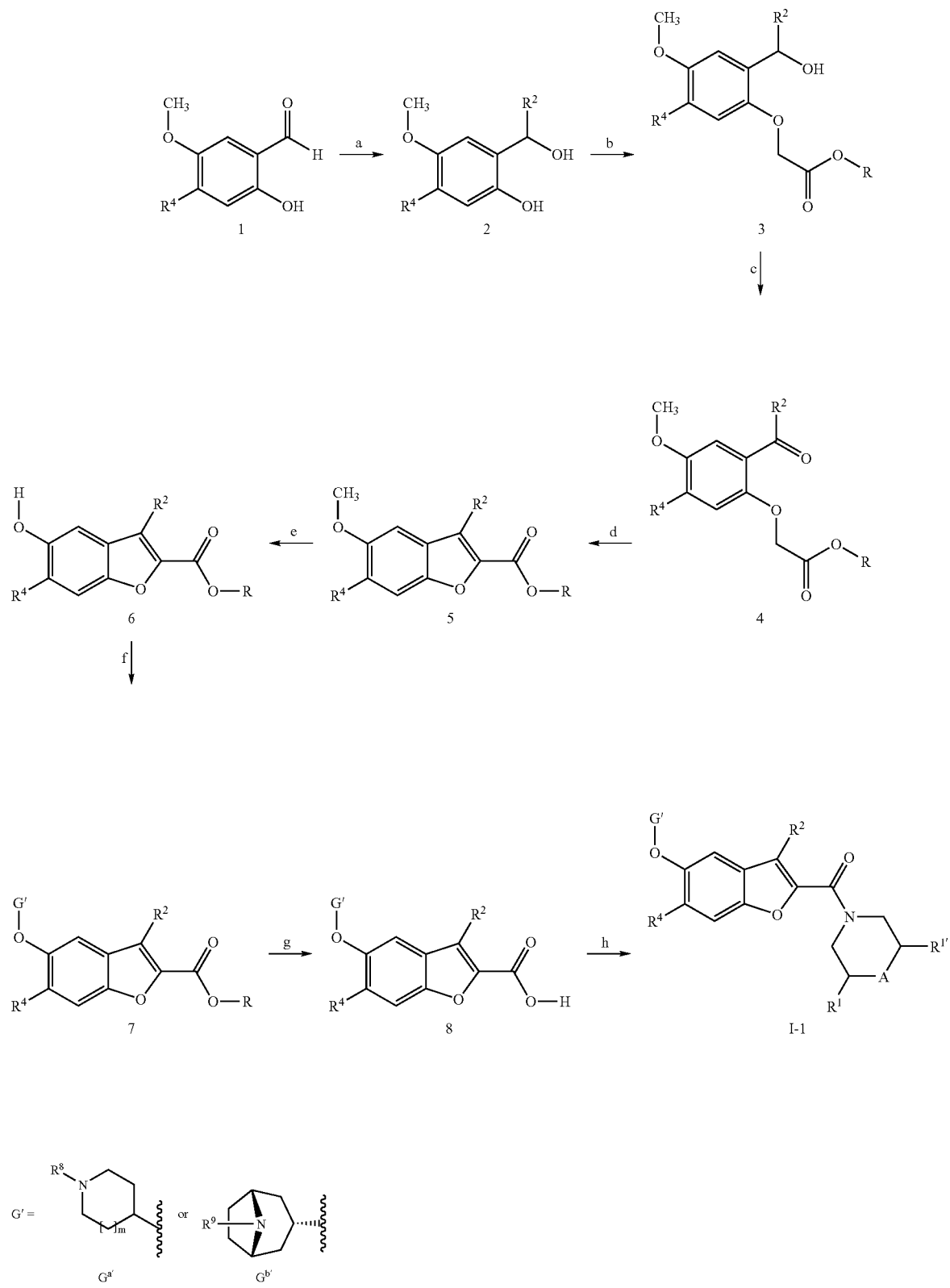
Scheme 1

Salicylaldehydes 1 (scheme 1) are reacted with two eq. of a metalorganic reagent, e.g., a Grignard reagent $R^2Mg$—X or a Li derivative $R^2$—Li, in an inert solvent like THF at a temperature between $-78°$ C. and RT, to yield alcohol 2 (scheme 1, step a) which is then selectively alkylated at the phenolic OH with alkyl bromoacetate in the presence of a base, e.g., $Cs_2CO_3$ or $K_2CO_3$, in a suitable solvent like acetonitrile or acetone, to produce intermediate 3 (scheme 1, step b). The latter is then oxidized with, e.g., $MnO_2$ in $CH_2Cl_2$ or tetrapropylammonium perrhutenate and N-methylmorpholine N-oxide as stoichiometric oxidant (St. Ley et al., *Synthesis* (1994), (7), 639-66) in a solvent like $CH_2Cl_2$, preferably in the presence of molecular sieves, to furnish ketone 4 (scheme 1, step c). Ensuing cyclocondensation is then induced by treatment with a strong base, e.g., KOtBu in a solvent like 1,2-dimethoxyethane in a temperature range between $-30°$ C. and $+30°$ C. (scheme 1, step d). Depending upon the exact reaction conditions, the corresponding aldolproduct is also— or sometimes almost exclusively—obtained which can then be transformed into 5 by brief treatment with a strong acid like, e.g., conc. sulphuric acid. Alternatively, this dehydration can also be postponed to the next step, namely cleavage of the aromatic methylether with a reagent typically used for such a transformation like $BBr_3$ in a solvent like $CH_2Cl_2$ (scheme 1, step e). Employing a larger amount of reagent leads to concomitant ether cleavage and dehydrative aromatisation. Phenol 6 is then subjected to a Mitsunobu reaction by treatment with alcohol G'—OH in the presence of a trialkylphosphine or triphenylphosphine and of an azo compound like diethyl azodicarboxylate (DEAD) or diisopropyl azodicarboxylate (DIAD) in an inert solvent like THF to yield key intermediate 7 (scheme 1, step f). Hydrolysis with a strong inorganic base like, e.g., NaOH or LiOH in a solvent or solvent mixture containing water, THF, EtOH or MeOH in a temperature range between $0°$ C. and RT generates acid 8 (scheme 1, step g) which is finally coupled with the suitable amine under standard conditions like, e.g., BOP ((benzotriazol-1-yloxy)-tris-(dimethylamino)-phosphonium hexafluorophosphate) and N-diisopropyletylamine to give, eventually, compound I-1 (scheme 1, step g).

In case $R^8$ within $G^a$ is an alkoxycarbonyl group, preferably a tert-butyloxycarbonyl, this protecting group of 7b can be removed (scheme 2, step i) by acid treatment, e.g., HCl or trifluoroacetic acid (see "Protective Groups in Organic Synthesis", T. W. Greene, Wiley-Interscience, 1999) to yield free amine 7c. Reductive amination under standard conditions, employing a suitable reducing agent such as py-$BH_3$ complex, $NaBH(OAc)_3$, $NaCNBH_3$ under acidic (e.g., acetic acid or $Ti(iPrO)_4$ or $ZnCl_2$ as additive) in a solvent such as $CH_2Cl_2$, dichloroethane (DCE), ethanol, isopropanol or mixtures thereof delivers intermediate 7d which is then further processed as described above. In this and in all following reaction schemes, the order of steps can also be reversed: ester 5 can first be hydrolysed to the free acid and then coupled with the suitable amine to form the corresponding amide, before the phenolic OH group is liberated and subjected to the Mitsunobu reaction.

Scheme 2

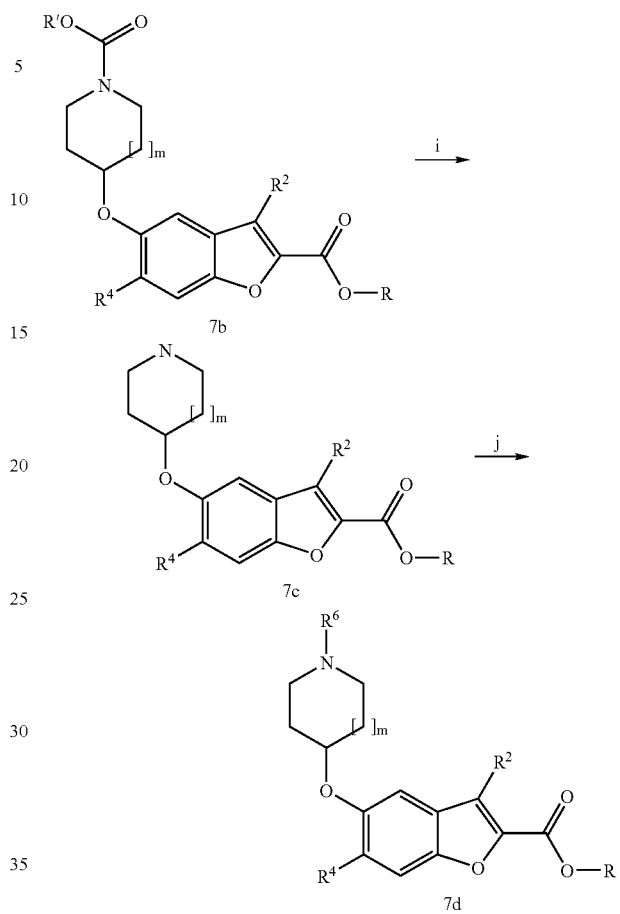

The necessary starting aldehydes are either commercially available, known from the literature, or can be prepared according to scheme 3. Thereby, the electron rich aromatic compound 1 is subjected to a Vilsmeier-Haack reaction (A. Vilsmeier and A. Haack, *Ber.* 60, 119 (1937)) with, e.g., $POCl_3$ and N-methylformanilide with or without solvent, e.g. DMF, to furnish aldehyde 2. Regioselective cleavage of the ortho-methoxy group is then achieved by treatment with $AlCl_3$ and NaI in acetonitrile to provide the desired salicylaldehyde 3 (Lanfranchi, Don Antoine; Hanquet, Gilles, *Journal of Organic Chemistry* (2006), 71(13), 4854-4861).

Scheme 3

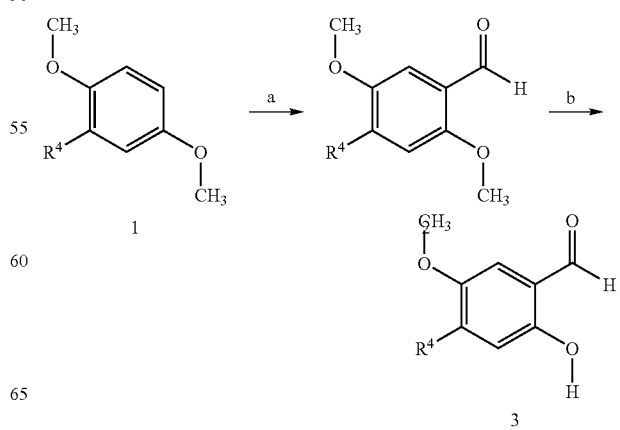

The regioisomeric benzofurans wherein $R^4$ is G can be prepared in perfect analogy which does not need further comment. For the sake of completeness, it is nevertheless summarized in scheme 4.
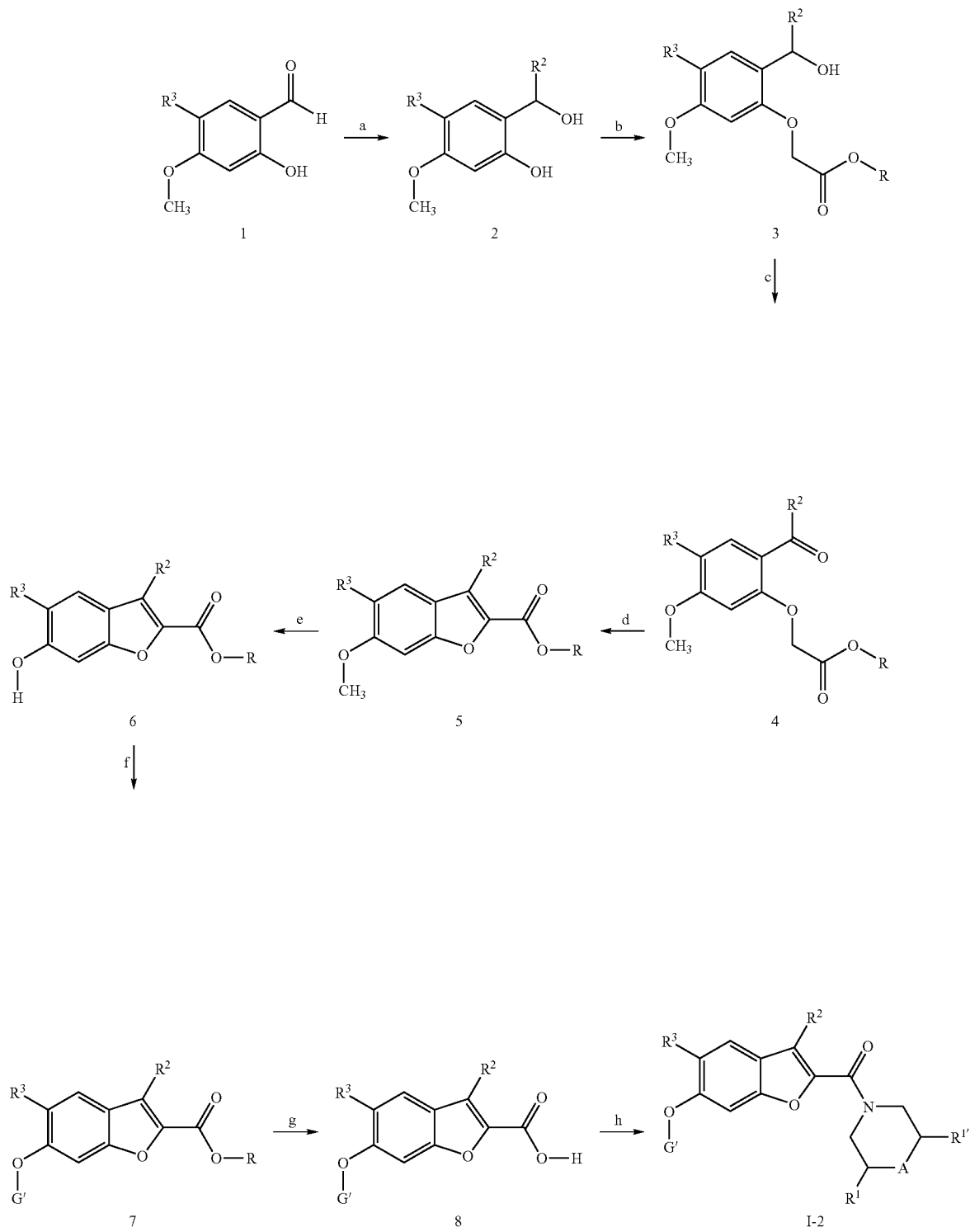

Alternatively, compounds of the general formula I wherein $R^4$ is G can be accomplished according to scheme 5. Thereby, a resorcinol 1 is subjected to a Friedel-Crafts type reaction with an acid $R_2COOH$ and a strong Lewis acid, e.g., $BF_3$ etherate, typically without solvent at 90-140° C. to form ketone 2 (WO 2004/072051, scheme 5, step a). The more reactive OH group can then selectively be alkylated by treatment with methyl iodide and a base, typically $Cs_2CO_3$ or $K_2CO_3$, in a suitable solvent like acetonitrile or acetone, to yield monomethyl ether 3 (T. Reichstein et al., *Helv. Chimica Acta* (1935), 18, 816-30, scheme 5, step b). The following steps c-h are then performed in perfect analogy to those described in scheme 1 and 4 leading to compounds of general formula I.

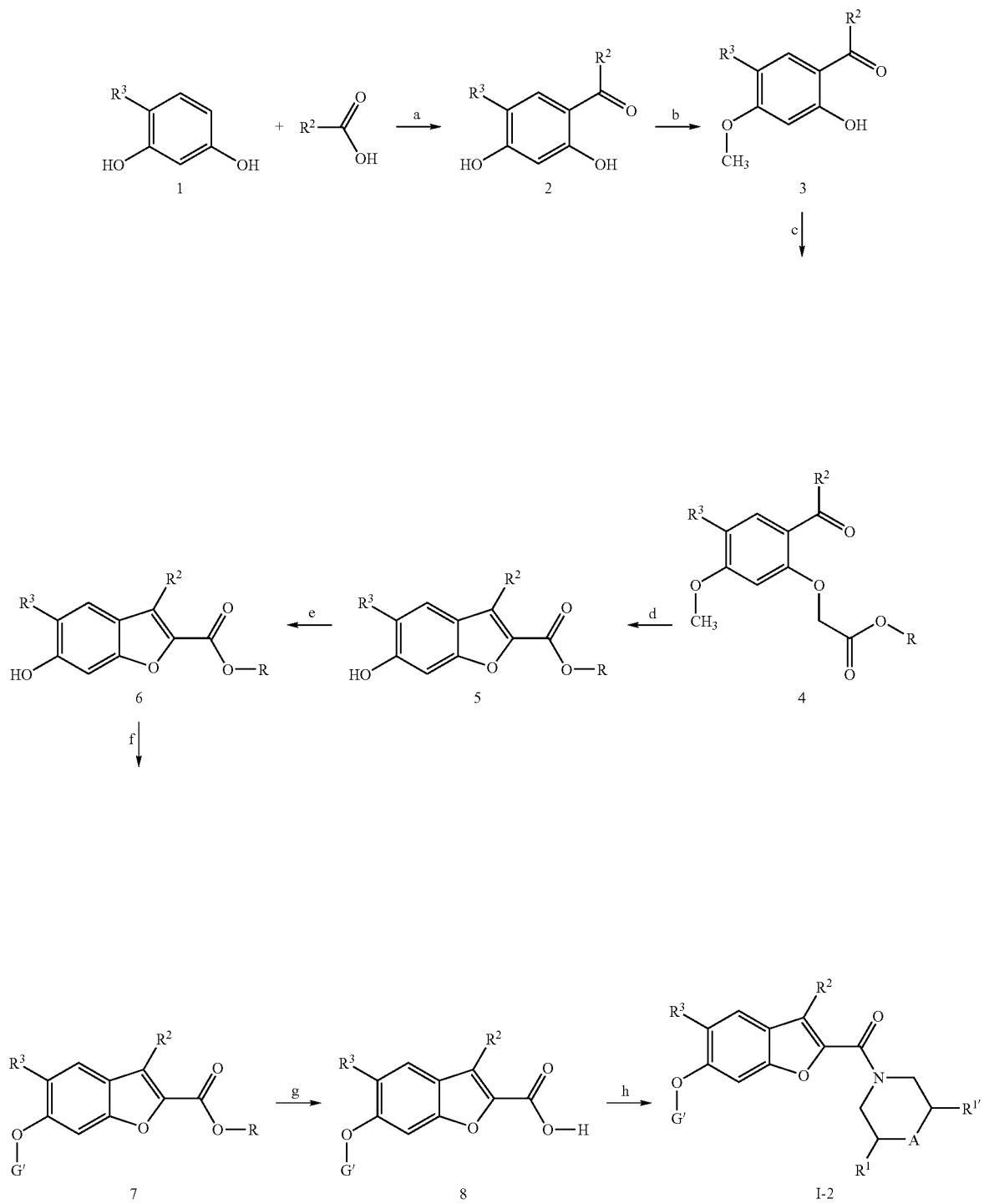

Scheme 5

The compounds of formula I can also be prepared according to scheme 6 in an analogous manner but starting with a hydroquinone 1; however, the first step needs slightly harsher reaction conditions.

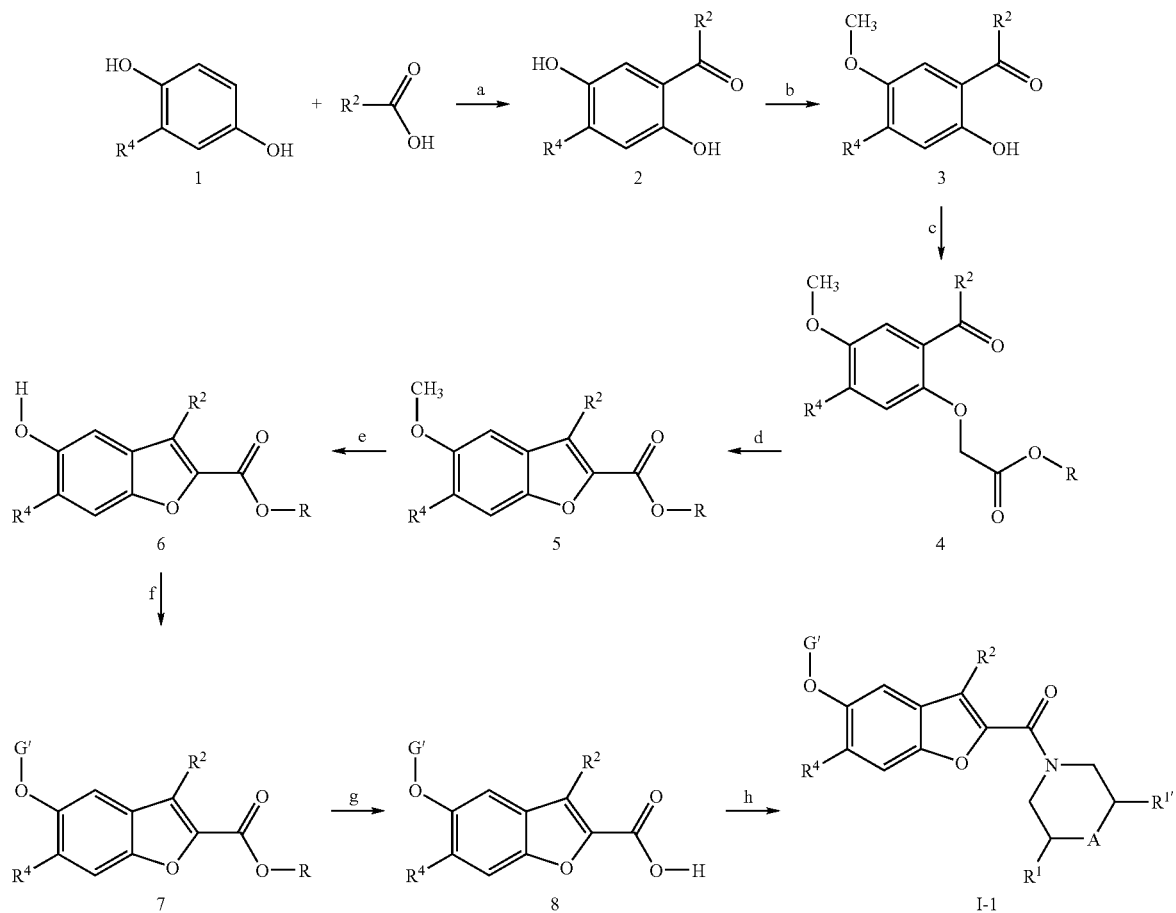

Scheme 6

Alternatively, the compounds of formula I can also be prepared according to scheme 7 starting with a resorcinol dimethylether 1. Classical Friedel-Crafts acylation with an acyl halogenide $R^2COCl$ in the presence of a Lewis acid like, e.g., $AlCl_3$, in an inert solvent like $CH_2Cl_2$ in a temperature range between −30° C. and +30° C. delivers intermediate 2. Regioselective cleavage of the ortho methoxy group by treatment with $AlCl_3$ and NaI in acetonitrile works equally well with ketones (Lanfranchi, Don Antoine; Hanquet, Gilles, *Journal of Organic Chemistry* (2006), 71(13), 4854-4861) and furnishes phenol 3. The remaining steps c-h are then performed as discussed above.

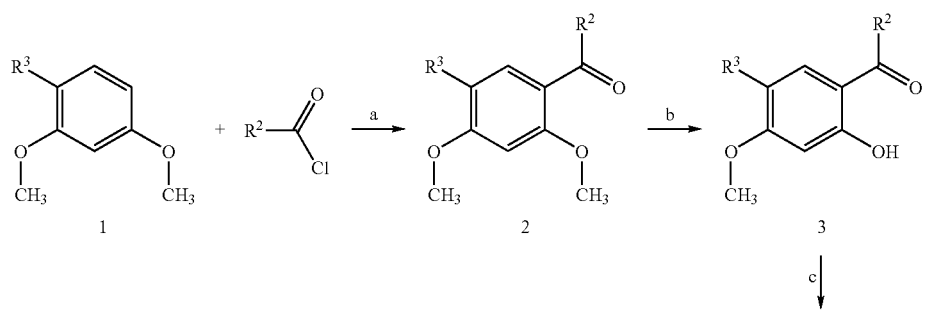

Scheme 7

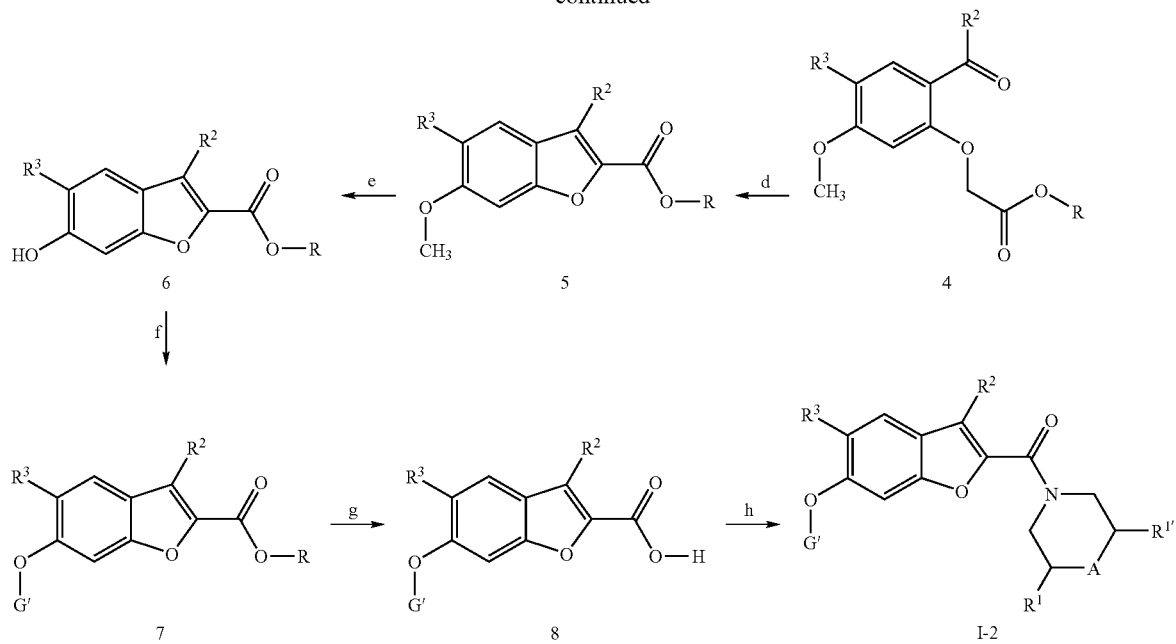

Compounds of formula I (X=S, R²=H) can be prepared according to scheme 8 starting with a 2-fluoro-4-methoxy-benzaldehyde. Reaction with a thioglycolic acid alkyl ester in presence of a base like NaH or K₂CO₃ or triethylamine in a polar solvent like THF or DMSO in a temperature range of 20-100° C. renders the desired benzothiophenes 2 (scheme 8, step a, cf. A. J. Bridges et al., *Tetrahedron Letters* 1992, 33(49), 7499-502; T. Gallagher et al., *Tetrahedron Letters* 2000, 41(28), 5415-5418; A. J. Bridges et al., *Bioorganic & Medicinal Chemistry* 1993, 1(6), 403-10). Ensuing cleavage of the aromatic methylether is then performed with a reagent typically used for such a transformation like BBr₃ in a solvent like CH₂Cl₂ (scheme 8, step b). Phenol 3 is then subjected to a Mitsunobu reaction by treatment with alcohol G'—OH in the presence of a trialkylphosphine or triphenylphosphine and of an azo compound like diethyl azodicarboxylate (DEAD) or diisopropyl azodicarboxylate (DIAD) in an inert solvent like THF to yield key intermediate 4 (scheme 8, step c). Hydrolysis with a strong inorganic base like, e.g., NaOH or LiOH in a solvent or solvent mixture containing water, THF, EtOH or MeOH in a temperature range between 0° C. and RT generates acid 5 (scheme 8, step d) which is finally coupled with the suitable amine under standard conditions like, e.g., BOP ((benzotriazol-1-yloxy)-tris-(dimethylamino)-phosphonium hexafluorophosphate) and N-diisopropylethylamine to give, finally, compound I-3 (scheme 8, step e).

Scheme 8

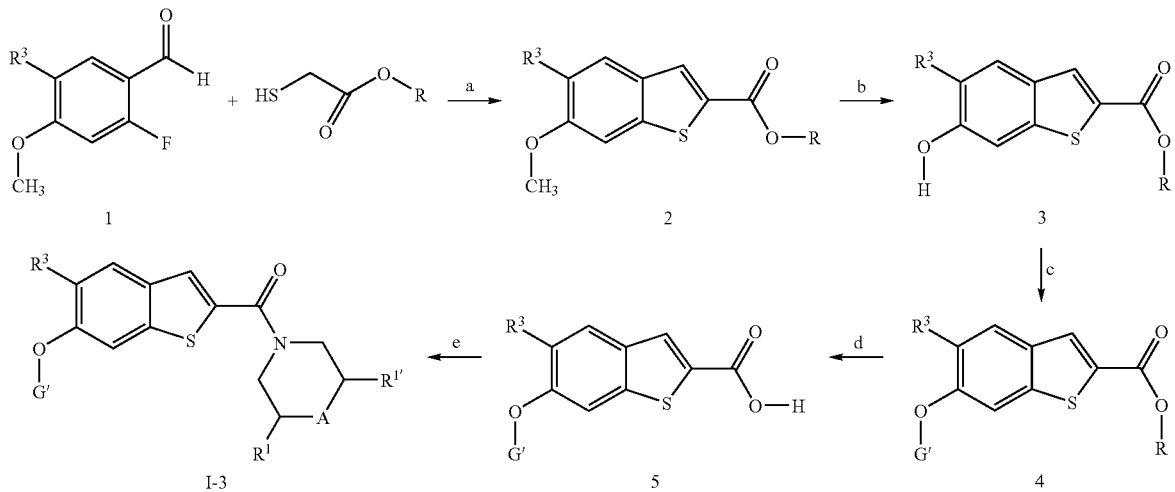

The regioisomeric benzothiophens I wherein $R^3$ is G can be prepared in perfect analogy which does not need further comment. For the sake of completeness, it is nevertheless summarized in scheme 9.

In another preferable aspect, the expression 'diseases associated with modulation of H3 receptors' relates to CNS disorders such as sleep disorders (insomnia).

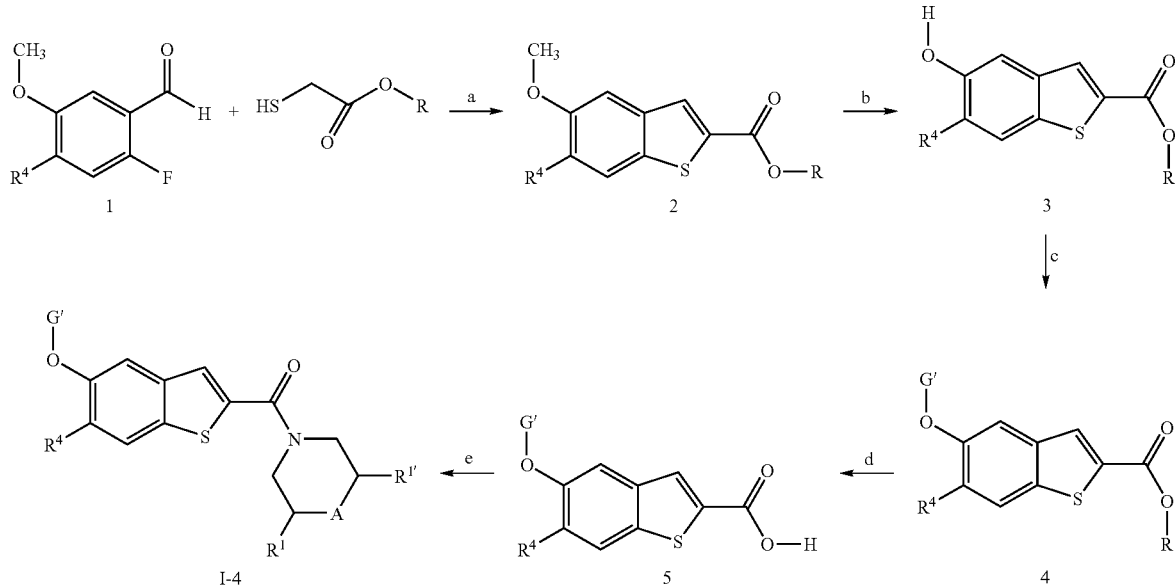

Scheme 9

The compounds of formula I can contain several asymmetric centres and can be present in the form of optically pure enantiomers, mixtures of enantiomers such as, e.g. racemates, optically pure diastereomers, mixtures of diastereomers, diastereomeric racemates or mixtures of diastereomeric racemates. The optically active forms can be obtained for example by resolution of the racemates, by asymmetric synthesis or asymmetric chromatography (chromatography with a chiral adsorbent or eluant).

As described above, the compounds of formula I of the present invention can be used as medicaments for the treatment and/or prevention of diseases which are associated with the modulation of H3 receptors.

In this context, the expression 'diseases associated with the modulation of H3 receptors' means diseases which can be treated and/or prevented by modulation of H3 receptors. Such diseases encompass, but are not limited to, obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastrointestinal disorders.

In a preferable aspect, the expression 'diseases associated with modulation of H3 receptors' relates to obesity, metabolic syndrome (syndrome X), and other eating disorders, with obesity being especially preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of H3 receptors.

In another embodiment, the invention relates to a method for the treatment and/or prevention of diseases which are associated with the modulation of H3 receptors, which method comprises administering a therapeutically active amount of a compound of formula I to a human being or animal. A method for the treatment and/or prevention of obesity is preferred.

The invention further relates to the use of compounds of formula I as defined above for the treatment and/or prevention of diseases which are associated with the modulation of H3 receptors.

In addition, the invention relates to the use of compounds of formula I as defined above for the preparation of medicaments for the treatment and/or prevention of diseases which are associated with the modulation of H3 receptors. The use of compounds of formula I as defined above for the preparation of medicaments for the treatment and/or prevention of obesity is preferred.

Furthermore, the present invention relates to the use of a compound of formula I for the manufacture of a medicament for the treatment and prevention of obesity in a patient who is also receiving treatment with a lipase inhibitor and particularly, wherein the lipase inhibitor is orlistat.

It is a further preferred object of the present invention to provide a method for the treatment or prevention of obesity and obesity related disorders which comprises administration of a therapeutically effective amount of a compound according to formula I in combination or association with a therapeutically effective amount of other drugs for the treatment of obesity or eating disorders so that together they give effective relief. Suitable other drugs include, but are not limited to, anorectic agents, lipase inhibitors, selective serotonin reuptake inhibitors (SSRI) and agents that stimulate metabolism of body fat. Combinations or associations of the above agents may be encompassing separate, sequential or simultaneous administration.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitors of lipases. Lipstatin is a natural product of microbial origin, and orlistat is the result of a hydrogenation of lipstatin. Other lipase inhibitors include a class of compounds commonly referred to as panclicins. Panclicins are analogues of orlistat (Mutoh et al, 1994). The term "lipase inhibitor" refers also to polymer bound lipase inhibitors for example described in International Patent Application WO 99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to tetrahydrolipstatin. Administration of a therapeutically effective amount of a compound according to formula I in combination or association with a therapeutically effective amount of tetrahydrolipstatin is especially preferred.

Tetrahydrolipstatin (orlistat) is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 0 185 359, 0 189 577, 0 443 449, and 0 524 495.

Suitable anorectic agents of use in combination with a compound of the present invention include, but are not limited to, APD356, aminorex, amphechloral, amphetamine, axokine, benzphetamine, bupropion, chlorphentermine, clobenzorex, cloforex, clominorex, clortermine, CP945598, cyclexedrine, CYT009-GhrQb, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, metreleptin, norpseudoephedrine, pentorex, phendimetrazine, phenmetrazine, phentermine, phenylpropanolamine, picilorex, rimonabant, sibutramine, SLV319, SNAP 7941, SR147778 (Surinabant), steroidal plant extract (e.g. P57) and TM30338 and pharmaceutically acceptable salts thereof.

Most preferable anorectic agents are sibutramine, rimonabant and phentermine.

Suitable selective serotonin reuptake inhibitors of use in combination with a compound of the present invention include: fluoxetine, fluvoxamine, paroxetine and sertraline, and pharmaceutically acceptable salts thereof.

Suitable agents that stimulate metabolism of body fat include, but are not limited to, growth hormone agonist (e.g. AOD-9604).

The use of a compound of formula I in the manufacture of a medicament for the treatment and prevention of obesity in a patient who is also receiving treatment with a compound selected from the group consisting of a lipase inhibitor, an anorectic agent, a selective serotonin reuptake inhibitor, and an agent that stimulates metabolism of body fat, is also an object of the present invention.

The use of a compound of formula I in the manufacture of a medicament for the treatment and prevention of obesity in a patient who is also receiving treatment with a lipase inhibitor, preferably with tetrahydrolipstatin, is also an object of the present invention.

It is a further preferred object to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of a lipase inhibitor, particularly, wherein the lipase inhibitor is tetrahydrolipstatin. Also an object of the invention is the method as described above for the simultaneous, separate or sequential administration of a compound according to formula I and a lipase inhibitor, particularly tetrahydrolipstatin.

It is a further preferred object to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of an anti-diabetic agent.

The term "anti-diabetic agent" refers to compounds selected from the group consisting of 1) PPARγ agonists such as pioglitazone (actos) or rosiglitazone (avandia), and the like; 2) biguanides such as metformin (glucophage), and the like; 3) sulfonylureas such as glibenclamide, glimepiride (amaryl), glipizide (glucotrol), glyburide (DiaBeta), and the like; 4) nonsulfonylureas such as nateglinide (starlix), repaglimide (prandin), and the like; 5) PPARα/γ agonists such as GW-2331, and the like 6) DPP-IV-inhibitors such as LAF-237 (vildagliptin), MK-0431, BMS-477118 (saxagliptin) or GSK23A and the like; 7) Glucokinase activators such as the compounds disclosed in e.g. WO 00/58293 A1, and the like; 8) α-Glucosidase inhibitors such as acarbose (precose) or miglitol (glyset), and the like.

Also an object of the invention is the method as described above for the simultaneous, separate or sequential administration of a compound according to formula I and a therapeutically effective amount of an anti-diabetic agent.

The use of a compound of formula I in the manufacture of a medicament for the treatment and prevention of Type II diabetes in a patient who is also receiving treatment with an anti-diabetic agent is also an object of the present invention.

It is a further preferred object to provide a method of treatment or prevention of dyslipidemia in a human which comprises administration of a therapeutically effective amount of a compound according to formula I in combination or association with a therapeutically effective amount of a lipid lowering agent.

The term "lipid lowering agent" refers to compounds selected from the group consisting of 1) bile acid sequestrants such as cholestyramine (questran), colestipol (colestid), and the like; 2) HMG-CoA reductase inhibitors such as atorvastatin (lipitor), cerivastatin (baycol), fluvastatin (lescol), pravastatin (pravachol), simvastatin (zocor) and the like; 3) cholesterol absorption inhibitors such as ezetimibe, and the like; 4) CETP inhibitors such as torcetrapib, JTT 705, and the like; 5) PPARα-agonists such as beclofibrate, gemfibrozil (lopid), fenofibrate (lipidil), bezafibrate (bezalip), and the like; 6) lipoprotein synthesis inhibitors such as niacin, and the like; and 7) niacin receptor agonists such as nicotinic acid, and the like.

Also an object of the invention is the method as described above for the simultaneous, separate or sequential administration of a compound according to formula I and a therapeutically effective amount of a lipid lowering agent.

The use of a compound of formula I in the manufacture of a medicament for the treatment and prevention of dyslipidemia in a patient who is also receiving treatment with a lipid lowering agent, is also an object of the present invention.

It is a further preferred object to provide a method of treatment or prevention of hypertension in a human which comprises administration of a therapeutically effective amount of a compound according to formula I in combination or association with a therapeutically effective amount of an anti-hypertensive agent.

The term "anti-hypertensive agent" or "blood-pressure lowering agent" refers to compounds selected from the group consisting of 1) Angiotensin-converting Enzyme (ACE) Inhibitors including benazepril (lotensin), captopril (capoten), enalapril (vasotec), fosinopril (monopril), lisinopril (prinivil, zestril), moexipril (univasc), perindopril (coversum), quinapril (accupril), ramipril (altace), trandolapril (mavik), and the like; 2) Angiotensin 11 Receptor Antagonists including candesartan (atacand), eprosartan (teveten), irbesartan (avapro), losartan (cozaar), telmisartan (micadisc), valsartan (diovan), and the like; 3) Adrenergic Blockers (peripheral or central) such as the beta-adrenergic blockers including acebutolol (sectrol), atenolol (tenormin), betaxolol (kerlone), bisoprolol (zebeta), carteolol (cartrol), metoprolol (lopressor; toprol-XL), nadolol (corgard), penbutolol (levatol), pindolol (visken), propranolol (inderal), timolol (blockadren) and the like; alpha/beta adrenergic blockers including carvedilol (coreg), labetalol (normodyne), and the like; alpha-1 adrenergic blockers including prazosin (minipress), doxazosin (cardura), terazosin (hytrin), phenoxybenzamine (dibenzyline), and the like; peripheral adrenergic-neuronal blockers including guanadrel (hylorel), guanethidine (ismelin), reserpine (serpasil), and the like; alpha-2 adrenergic blockers including a-methyldopa (aldomet), clonidine (catapres), guanabenz (wytensin), guanfacine (tenex), and the like; 4) Blood Vessel Dilators (Vasodilators) including hydralazine (apresoline), minoxidil (lonitren), clonidine (catapres), and the like; 5) Calcium Channel Blockers including amlodipine (norvasc), felodipine (plendil), isradipine (dynacirc), nicardipine (cardine sr), nifedipine (procardia, adalat), nisoldipine (sular), diltiazem (cardizem), verapamil (isoptil), and the like; 6) Diuretics such as thiazides and thiazides-like agents, including hydrochlorothiazide (hydrodiuril, microzide), chlorothiazide (diuril), chlorthalidone (hygroton), indapamide (lozol), metolazone (mykrox), and the like; loop diuretics, such as bumetanide (bumex) and furosemide (lasix), ethacrynic acid (edecrin), torsemide (demadex), and the like; potassium-sparing diuretics including amiloride (midamor), triamterene (dyrenium), spironolactone (aldactone), and the tiamenidine (symcor) and the like; 7) Tyrosine Hydroxylase Inhibitors, including metyrosine (demser), and the like; 8) Neutral Endopeptidase Inhibitors, including BMS-186716 (omapatrilat), UK-79300 (candoxatril), ecadotril (sinorphan), BP-1137 (fasidotril), UK-79300 (sampatrilat) and the like; and 9) Endothelin Antagonists including tezosentan, A308165, and the like.

Also an object of the invention is the method as described above for the simultaneous, separate or sequential administration of a compound according to formula I and a therapeutically effective amount of an anti-hypertensive agent.

The use of a compound of formula I in the manufacture of a medicament for the treatment and prevention of hypertension in a patient who is also receiving treatment with an anti-hypertensive agent, is also an object of the present invention.

As described above, the compounds of formula I and their pharmaceutically acceptable salts possess valuable pharmacological properties. Specifically, it has been found that the compounds of the present invention are good histamine 3 receptor (H3R) antagonists and/or inverse agonists.

The following test was carried out in order to determine the activity of the compounds of formula I.

Binding Assay with $^3$H—(R)α-methylhistamine

Saturation binding experiments were performed using HR3-CHO membranes prepared as described in Takahashi, K, Tokita, S., Kotani, H. (2003) J. Pharmacol. Exp. Therapeutics 307, 213-218.

An appropriate amount of membrane (60 to 80 µg protein/well) was incubated with increasing concentrations of $^3$H(R)α-Methylhistamine di-hydrochloride (0.10 to 10 nM). Non specific binding was determined using a 200 fold excess of cold (R)α-Methylhistamine dihydrobromide (500 nM final concentration). The incubation was carried out at room temperature (in deep-well plates shaking for three hours). The final volume in each well was 250 µl. The incubation was followed by rapid filtration on GF/B filters (pre-soaked with 100 µl of 0.5% PEI in Tris 50 mM shaking at 200 rpm for two hours). The filtration was made using a cell-harvester and the filter plates were then washed five times with ice cold washing buffer containing 0.5 M NaCl. After harvesting, the plates were dried at 55° C. for 60 min, then scintillation fluid (Microscint 40, 40 microl in each well) was added and the amount of radioactivity on the filter was determined in Packard topcounter after shaking the plates for two hours at 200 rpm at room temperature.

Binding Buffer: 50 mM Tris-HCl pH 7.4 and 5 mM $MgCl_2 \times 6H_2O$ pH 7.4. Washing Buffer: 50 mM Tris-HCl pH 7.4 and 5 mM $MgCl_2 \times 6H_2O$ and 0.5 M NaCl pH 7.4.

Indirect measurement of affinity of H3R inverse agonists: twelve increasing concentrations (ranging from 10 µM to 0.3 nM) of the selected compounds were always tested in competition binding experiments using membranes of the human HR3-CHO cell line. An appropriate amount of protein, e.g. approximately 500 cpm binding of RAMH at Kd, were incubated for 1 hour at room temperature in 250 µl final volume in 96-well plates in presence of $^3$H(R)α-Methylhistamine (1 nM final concentration=Kd). Non-specific binding was determined using a 200 fold excess of cold (R)α-Methylhistamine dihydrobromide.

All compounds were tested at a single concentration in duplicate. Compounds that showed an inhibition of [$^3$H]-RAMH by more than 50% were tested again to determine $IC_{50}$ in a serial dilution experiment, meaning concentrations were spanning 10 points starting from $4.6 \times 10^{-6}$ M to $1.0 \times 10^{-9}$ M. The dilution factor was 1/2.15 for the whole series. The concentration at which 50% inhibition of the radioligand $^3$H(R)α-methylhistamine is obtained (the $IC_{50}$) is determined from the linear regression of a plot of the logarithm of the concentration versus percent inhibition measured for the different concentrations. Ki's were calculated from $IC_{50}$ based on Cheng-Prusoff equation (Cheng, Y, Prusoff, W H (1973) Biochem Pharmacol 22, 3099-3108): $Ki=IC_{50}/[1+D/Kd]$ wherein D is the concentration of the radioligand and Kd is the binding constant for the radioligand binding to the receptor under the conditions used in the competition experiment.

The compounds of the present invention exhibit $K_i$ values within the range of about 1 nM to about 1000 nM, preferably of about 1 nM to about 100 nM, and more preferably of about 1 nM to about 30 nM, most preferably of about 1 nM to about 20 nM. The following table shows measured values for some selected compounds of the present invention.

|  | $K_i$ (nM) |
|---|---|
| Example 17 | 1.3 |
| Example 45 | 0.4 |
| Example 65 | 0.1 |
| Example 69 | 1.5 |
| Example 72 | 0.8 |
| Example 76 | 0.5 |
| Example 82 | 0.4 |
| Example 91 | 2.6 |
| Example 94 | 2.3 |

Demonstration of additional biological activities of the compounds of the present invention may be accomplished through in vitro, ex vivo, and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoAl mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein, and serum triglyceride levels are determined.

Method for Measuring HDL-Cholesterol Levels

To determine plasma HDL-cholesterol levels, hApoAl mice are bled and grouped with equivalent mean plasma HDL-cholesterol-levels. The mice are orally dosed once daily with vehicle or test compound for 7 to 14 days, and then bled on the following day. Plasma is analyzed for HDL-cholesterol.

The compounds of formula I and their pharmaceutically acceptable alts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable salts into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula I.

The following examples serve to illustrate the present invention in more detail. They are, however, not intended to limit its scope in any manner.

EXAMPLES

Example 1

(1,1-Dioxo-$_1\lambda$6-thiomorpholin-4-yl)-[5-(1-isopropyl-piperidin-4-yloxy)-benzofuran-2-yl]-methanone Step 1: (2-Formyl-4-methoxy-phenoxy)-acetic acid ethyl ester To a solution of 2-hydroxy-5-methoxybenzaldehyde (21.75 g, 143 mmol) in 240 mL acetonitrile were successively added $Cs_2CO_3$ (55.9 g, 1.2 eq.) and ethyl bromoacetate (16.6 mL, 1.05 eq.) and the mixture vigorously stirred at ambient temperature for 2 h. Pouring onto crashed ice/$NH_4Cl$, twofold extraction with AcOEt, washing with water and brine, drying over magnesium sulfate, and evaporation of the solvents left 34.36 g of the title product, sufficiently pure to be used for the next step.

Step 2: 5-Methoxy-benzofuran-2-carboxylic acid ethyl ester

The above prepared (2-formyl-4-methoxy-phenoxy)-acetic acid ethyl ester (34.36 g, 144 mmol) was dissolved in 340 mL of dimethoxyethane and treated at −15° C. with KOtBu (6.47 g, 0.4 eq.). After 15 Min., the reaction mixture was poured onto crashed ice/NH$_4$Cl, twofold extracted with AcOEt, washed with water and brine, dried over magnesium sulfate, and evaporated to dryness. Flash chromatography (SiO$_2$, hexane/AcOEt=9/1) gave finally 8.10 g of the title compound as white crystals.

MS (ISP): 221.1 [M+H]$^+$.

Step 3: 5-Hydroxy-benzofuran-2-carboxylic acid ethyl ester

The above prepared 5-methoxy-benzofuran-2-carboxylic acid ethyl ester (8.10 g, 36.8 mmol) was dissolved in 250 mL of CH$_2$Cl$_2$, cooled to 0° C., and treated with BBr$_3$ (73.6 mL of 1M solution in CH$_2$Cl$_2$, 2 eq.). After 2 h, the reaction mixture was carefully poured onto crashed ice, twofold extracted with CH$_2$Cl$_2$, washed with brine, dried over magnesium sulfate, and evaporated to dryness. Ensuing flash chromatography (SiO$_2$, hexane/AcOEt=8/2) delivered then 5.63 g of the title compound as off-white crystals.

MS (ISP): 205.4 [M−H]$^−$.

Step 4: 5-(1-Isopropyl-piperidin-4-yloxy)-benzofuran-2-carboxylic acid ethyl ester The above prepared 5-hydroxy-benzofuran-2-carboxylic acid ethyl ester (1.50 g, 7.27 mmol) was dissolved in 36 mL of THF and treated successively at 10° C. with 1-isopropyl-piperidin-4-ol (1.46 g, 1.4 eq.), triphenylphosphine (2.67 g, 1.4 eq.) and DIAD (2.00 mL, 1.4 eq.), and the mixture then kept at ambient temperature for another 3 h. Pouring onto crashed ice/NH$_4$Cl, twofold extraction with AcOEt, washing with water and brine, drying over magnesium sulfate, and evaporation of the solvents, followed by flash chromatography (SiO$_2$, NEt$_3$/AcOEt=2/98), yielded finally 1.36 g of the title compound as light yellow oil.

MS (ISP): 332.3 [M+H]$^+$.

Step 5: 5-(1-Isopropyl-piperidin-4-yloxy)benzofuran-2-carboxylic acid

The above prepared 5-(1-isopropyl-piperidinyloxy)-benzofuran-2-carboxylic acid ethyl ester (1.30 g, 3.92 mmol) was dissolved in 6.8 mL of THF/ethanol=1/1 and treated with 1.70 mL of aq. NaOH (3M, 1.3 eq.). The mixture was stirred for 2 h at ambient temperature and was then neutralized by adding 2.55 mL of 2M HCl (1.3 eq.). Careful evaporation of all solvents and drying afforded then 1.625 g of the title compound as off-white solid, contaminated with innocouos inorganic salts.

MS (ISP): 302.3 [M−H]$^−$.

Step 6: (1,1-Dioxo-$_1$λ6-thiomorpholin-4-yl)[5-(1-isopropyl-piperidin-4-yloxy)-benzofuran-2-yl]-methanone In a flask were mixed together the above prepared 5-(1-isopropyl-piperidin-4-yloxy)-benzofuran-2-carboxylic acid (1.25 g, 3.92 mmol, calculated as 73%), thiomorpholine 1,1-dioxide (0.636 g, 1.2 eq.), (benzotriazol-1-yloxy)-tris-(dimethylamino)phosphonium hexafluorophosphate (2.081 g, 1.2 eq.) and 2.4 eq. of N-ethyldiisopropylamine (1.60 mL) in 24 mL of abs. THF and allowed to react during one night at ambient temperature. Pouring onto crashed ice/AcOEt/NH$_4$Cl-solution, twofold extraction with AcOEt, washing with water and brine, drying over magnesium sulfate, and evaporation of the solvents, followed by flash chromatography (SiO$_2$, NEt$_3$/AcOEt=2/98) and trituration in hexane/AcOEt=7/3 yielded 1.192 g of the title compound as off-white crystals.

MS (ISP): 421.1 [M+H]$^+$.

Example 2

(cis-2,6-Dimethyl-morpholin-4-yl)-[5-(1-isopropyl-piperidin-4-yloxy)-benzofuran-2-yl]-methanone Step 1: 5-Methoxy-benzofuran-2-carboxylic acid The above prepared 5-methoxy-benzofuran-2-carboxylic acid ethyl ester (0.500 g, 2.27 mmol) was dissolved in 4.6 mL of THF/ethanol=1/1 and treated with 2.27 mL of aq. NaOH (3M, 3 eq.). The mixture was stirred for 2 h at ambient temperature and was then poured onto crashed ice/AcOEt/HCl dil.; the organic layer was washed with water, dried over sodium sulfate, and evaporated to dryness to leave 0.428 g of the title acid as off-white solid.

Step 2: ((cis)-2,6-Dimethyl-morpholin-4-yl)-(5-methoxy-benzofuran-2-yl)-methanone In a flask were mixed together the above prepared 5-methoxy-benzofuran-2-carboxylic acid (0.428 g, 2.23 mmol), cis-2,6-dimethylmorpholine (0.308 g, 1.2 eq.), (benzotriazol-1-yloxy)-tris-(dimethylamino)phosphonium hexafluorophosphate (1.18 g, 1.2 eq.) and 2.4 eq. of N-ethyl-diisopropylamine (0.915 mL) in 9 mL of abs. THF and allowed to react during one night at ambient temperature. Pouring onto crashed ice/AcOEt/NH$_4$Cl-solution, twofold extraction with AcOEt, washing with water and brine, drying over magnesium sulfate, and evaporation of the solvents, followed by flash chromatography (SiO$_2$, hexane/AcOEt=7/3 generated 0.614 g of the title compound as colorless oil.

MS (ISP): 290.0 [M+H]$^+$.

Step 3: ((cis)-2,6-Dimethyl-morpholin-4-yl)-(5-hydroxy-benzofuran-2-yl)-methanone The above prepared ((cis)-2,6-dimethyl-morpholin-4-yl)-(5-methoxy-benzofuran-2-yl)-methanone (0.614 g, 2.12 mmol) was dissolved in 14 mL of CH$_2$Cl$_2$, cooled to 0° C., and treated with BBr$_3$ (4.24 mL of 1M solution in CH$_2$Cl$_2$, 2 eq.). After 1 additional h at RT, the reaction mixture was carefully poured onto crashed ice, twofold extracted with AcOEt, washed with water, dried over sodium sulfate, and evaporated to dryness. Ensuing flash chromatography (SiO$_2$, hexane/AcOEt=1/1) yielded 0.556 g of the title compound as off-white solid.

MS (ISP): 274.4 [M+H]$^+$.

Step 4: ((cis)-2,6-Dimethyl-morpholin-4-yl)-[5-(1-isopropyl-piperidin-4-yloxy)-benzofuran-2-yl]-methanone The above prepared ((cis)-2,6-dimethyl-morpholin-4-yl)-(5-hydroxy-benzofuran-2-yl)-methanone (0.150 g, 0.545 mmol) was dissolved in 2.7 mL of THF and treated successively at 10° C. with 1-isopropyl-piperidin-4-ol (0.156 g, 2 eq.), triphenylphosphine (0.285 g, 2 eq.) and DIAD (0.212 mL, 2 eq.), and the mixture then kept at ambient temperature for another 3 h. Pouring onto crashed ice/NH$_4$Cl, twofold extraction with AcOEt, washing with water, drying over sodium sulfate, and evaporation of the solvents, followed by two flash chromatographies (SiO$_2$, NEt$_3$/AcOEt=4/96 and CH$_2$Cl$_2$/MeOH=9/1), yielded eventually 0.140 g of the title compound as colorless oil.

MS (ISP): 401.3 [M+H]$^+$.

Example 3

(4-Isopropyl-piperazin-1-yl)-[5-(1-isopropyl-piperidin-4-yloxy)-benzofuran-2-yl]-methanone In a flask were mixed together the above prepared 5-(1-isopropyl-piperidin-4-yloxy)-benzofuran-2-carboxylic acid (0.220 g, 0.549 mmol, corrected for purity), 1-isopropylpiperazine (0.084 g, 1.2 eq.), (benzotriazol-1-yloxy)-tris-(dimethylamino)-phosphonium hexafluorophosphate (0.291 g, 1.2 eq.) and 2.4 eq. of N-ethyldiisopropyl-amine (0.225 mL) in 2.2 mL of abs. THF and allowed to react during one night at ambient temperature. Pouring onto crashed ice/AcOEt/NH$_4$Cl-solution, twofold extraction with AcOEt, washing with water, drying over sodium sulfate, and evaporation of the solvents, followed by flash chromatography (SiO$_2$, NEt$_3$/AcOEt=4/96) produced 0.127 g of the title compound as light yellow oil.

MS (ISP): 414.3 [M+H]$^+$.

Example 4

(4,4-Difluoro-piperidin-1-yl)-[5-(1-isopropyl-piperidin-4-yloxy)-benzofuran-2-yl]-methanone The title compound was prepared in analogy to example 1, but using in step 6 4,4-difluoropiperidine instead of thiomorpholine 1,1-dioxide, as light yellow solid.

MS (ISP): 407.2 [M+H]$^+$.

Example 5

4-[5-(1-Isopropyl-piperidin-4-yloxy)-benzofuran-2-carbonyl]-piperazine-1-carboxylic acid tert-butyl ester This compound was prepared in analogy to example 1, but using in step 6 1-tert-butoxycarbonyl-piperazine instead of thiomorpholine 1,1-dioxide, as white solid.

MS (ISP): 472.1 [M+H]$^+$.

Example 6

(4,4-Difluoro-piperidin-1-yl)-[5-(1-isopropyl-piperidin-4-yloxy)-benzo[b]thiophen-2-yl]-methanone Step 1: a] 5-Methoxy-benzo[b]thiophene-2-carboxylic acid ethyl ester To a solution of 2-fluoro-5-methoxybenzaldehyde (21.70 g, 141 mmol) in 280 mL of DMSO were successively added K$_2$CO$_3$ (21.4 g, 1.1 eq.) and ethyl thioglycolate (17.07 mL, 1.1 eq.), and the mixture was vigorously stirred at 50° C. for 5 h. After cooling, the reaction mixture was poured onto crashed ice/HCl, twofold extracted with AcOEt, washed with water and brine, dried over magnesium sulfate, and evaporated. Flash chromatography (SiO$_2$, hexane/AcOEt=85/15) yielded in the less polar fractions 6.40 g of the title compound as light yellow solid and in the more polar ones 19.27 g of [(2-fluoro-4,5-Dimethoxy-phenyl)-hydroxy-methylsulfanyl]-acetic acid ethyl ester which can be recycled by stirring over night at 70° C. in DMSO in the presence of K$_2$CO$_3$.

Step 1: b] 5-Methoxy-benzo[b]thiophene-2-carboxylic acid methyl ester

To a solution of methyl thioglycolate (0.647 mL, 7.14 mmol, 1.1 eq.) in 14 mL of DMSO was added NaH 50% (0.405 g, 10.1 mmol, 1.56 eq.) and the mixture was stirred for 5 Min., before 2-fluoro-5-methoxybenzaldehyde (1.00 g, 6.49 mmol) was added (strongly exothermic). When the internal temperature had reached again 25° C., the reaction mixture was poured onto crashed ice and the precipitate filtered off and dried to obtain 0.199 g of the title compound as off-white solid.

MS (ISP): 223.1 [M+H]$^+$.

Step 2: 5-Hydroxy-benzo[b]thiophene-2-carboxylic acid methyl ester

The above prepared 5-methoxy-benzo[b]thiophene-2-carboxylic acid methyl ester (0.199 g, 0.895 mmol) was dissolved in 6 mL of CH$_2$Cl$_2$, cooled to 0° C., and treated with BBr$_3$ (1.79 mL of 1M solution in CH$_2$Cl$_2$, 2 eq.). After 2 additional h at 0° C., the reaction mixture was carefully poured onto crashed ice, twofold extracted with AcOEt, washed with water, dried over sodium sulfate, and evaporated to dryness. Flash chromatography (SiO$_2$, hexane/AcOEt=7/3) yielded 0.145 g of the title compound as off-white solid.

Step 3: 5-(1-Isopropyl-piperidin-4-yloxy)-benzo[b]thiophene-2-carboxylic acid methyl ester The above prepared 5-hydroxy-benzo[b]thiophene-2-carboxylic acid methyl ester (0.143 g, 0.687 mmol) was dissolved in 3.4 mL of THF and treated successively at 10° C. with 1-isopropyl-piperidin-4-ol (0.197 g, 2 eq.), triphenylphosphine (0.360 g, 2 eq.) and DIAD (0.267 mL, 2 eq.), and the mixture then kept at ambient temperature for another 2 h. Pouring onto crashed ice, twofold extraction with AcOEt, washing with water, drying over sodium sulfate, and evaporation of the solvents, followed by flash chromatography (SiO$_2$, NEt$_3$/AcOEt=5/95), delivered 0.222 g of the title compound as light yellow oil.

MS (ISP): 334.1 [M+H]$^+$.

Step 4: 5-(1-Isopropyl-piperidin-4-yloxy)-benzo[b]thiophene-2-carboxylic acid

The above prepared 5-(1-isopropyl-piperidin-4-yloxy)-benzo[b]thiophene-2-carboxylic acid methyl ester (0.222 g, 0.666 mmol) was dissolved in 1.3 mL of THF/ethanol=1/1 and treated with 0.333 mL of aq. NaOH (3M, 1.5 eq.). The mixture was stirred for 2 h at ambient temperature and was then neutralized by adding 0.50 mL of 2M HCl (1.5 eq.). Careful evaporation of all solvents, trituration in diethyl ether, and drying afforded then 0.256 g of the title compound as white solid, contaminated with innocouos inorganic salts.

MS (ISP): 318.4 [M−H]$^−$.

Step 5: (4,4-Difluoro-piperidin-1-yl)-[5-(1-isopropyl-piperidin-4-yloxy)-benzo[b]thiophen-2-yl]-methanone In a flask were mixed together the above prepared 5-(1-isopropyl-piperidin-4-yloxy)-benzo[b]thiophene-2-carboxylic acid (0.128 g, 0.333 mmol, corrected for purity), 4,4-difluoropiperidine hydrochloride (0.063 g, 1.2 eq.), (benzotriazol-1-yloxy)-tris-(dimethylamino)phosphonium hexafluorophosphate (0.181 g, 1.23 eq.) and 2.4 eq. of N-ethyldiisopropylamine (0.225 mL) in 1.3 mL of abs. THF and allowed to react during one night at ambient temperature. Pouring onto crashed ice/AcOEt/NH$_4$Cl-solution, twofold extraction with AcOEt, washing with water, drying over sodium sulfate, and evaporation of the solvents, followed by flash chromatography (SiO$_2$, NEt$_3$/AcOEt=4/96) produced 0.091 g of the title compound as light yellow solid.

MS (ISP): 423.2 [M+H]$^+$.

Example 7

(4,4-Difluoro-piperidin-1-yl)-[6-(1-isopropyl-piperidin-4-yloxy)benzo[b]thiophen-2-yl]-methanone Step 1: a] 6-Methoxy-benzo[b]thiophene-2-carboxylic acid methyl ester To a solution of methyl thioglycolate (1.29 mL, 14 mmol, 1.1 eq.) in 22 mL of DMSO was added NaH 50% (0.972 g, 20 mmol, 1.56 eq.) and the mixture was stirred for 5 Min., before 2-fluoro-4-methoxybenzaldehyde (2.00 g, 13 mmol) was added (strongly exothermic). When the internal temperature had reached again 25° C., the reaction mixture was poured onto crashed ice and the precipitate filtered off, washed with water, and dried to obtain 1.896 g of the title compound as light yellow crystals.

Step 2: 6-Hydroxy-benzo[b]thiophene-2-carboxylic acid methyl ester

The above prepared 6-methoxy-benzo[b]thiophene-2-carboxylic acid methyl ester (0.200 g, 0.900 mmol) was dissolved in 5.5 mL of $CH_2Cl_2$, cooled to 0° C., and treated with $BBr_3$ (1.90 mL of 1M solution in $CH_2Cl_2$, 2 eq.). After 3 additional h at ambient temperature, the reaction mixture was carefully poured onto crashed ice, twofold extracted with AcOEt, washed with water and brine, dried over magnesium sulfate, and evaporated to dryness. Flash chromatography ($SiO_2$, hexane/AcOEt=8/2) gave 0.061 g of the title compound as light brown solid.

Step 3: 6-(1-Isopropyl-piperidin-4-yloxy)-benzo[b]thiophene-2-carboxylic acid ethyl ester To 6-hydroxy-benzo[b]thiophene-2-carboxylic acid ethyl ester (0.300 g, 1.35 mmol, prepared as described above, but using ethyl instead of methyl thioglycolate), dissolved in 13.5 mL of THF, was added successively at 10° C. 1-isopropyl-piperidin-4-ol (0.387 g, 2 eq.), triphenylphosphine (0.708 g, 2 eq.) and DIAD (0.530 mL, 2 eq.), and the mixture then kept at this temperature for another 2 h. Pouring onto crashed ice, twofold extraction with AcOEt, washing with water and brine, drying over magnesium sulfate, and evaporation of all solvents, followed by flash chromatography ($SiO_2$, MeOH/AcOEt=1/9), delivered 0.360 g of the title compound as off-white solid.

MS (ISP): 348.3 $[M+H]^+$.

Step 4: 6-(1-Isopropyl-piperidin-4-yloxy)-benzo[b]thiophene-2-carboxylic acid

The above prepared 6-(1-isopropyl-piperidin-4-yloxy)-benzo[b]thiophene-2-carboxylic acid ethyl ester (0.359 g, 1.033 mmol) was dissolved in 2 mL of THF/ethanol=1/1 and treated with 0.517 mL of aq. NaOH (3M, 1.5 eq.). The mixture was stirred for 1 h at ambient temperature and was then neutralized by adding 0.77 mL of 2M HCl (1.5 eq.). Careful evaporation of all solvents and drying afforded then 0.475 g of the title compound as white solid contaminated with innocuous inorganic salts.

MS (ISP): 318.3 $[M-H]^-$.

Step 5: (4,4-Difluoro-piperidin-1-yl)-[6-(1-isopropyl-piperidin-4-yloxy)-benzo[b]thiophen-2-yl]-methanone In a flask were mixed together the above prepared 6-(1-isopropyl-piperidin-4-yloxy)-benzo[b]thiophene-2-carboxylic acid (0.147 g, 0.320 mmol, corrected for purity), 4,4-difluoropiperidine hydrochloride (0.060 g, 1.2 eq.), (benzotriazol-1-yloxy)-tris-(dimethylamino)phosphonium hexafluorophosphate (0.170 g, 1.2 eq.) and 2.5 eq. of N-ethyldiisopropylamine (0.760 mL) in 2 mL of abs. THF and allowed to react during one night at ambient temperature. Pouring onto crashed ice/AcOEt/$NH_4$Cl-solution, twofold extraction with AcOEt, washing with water and brine, drying over magnesium sulfate, and evaporation of the solvents, followed by flash chromatography ($SiO_2$, $CH_2Cl_2$/MeOH=9/1) produced 0.103 g of the title compound as white foam.

MS (ISP): 423.4 $[M+H]^+$.

Example 8

(4,4-Difluoro-piperidin-1-yl)-[3-isopropyl-6-(1-isopropyl-piperidin-4-yloxy)-benzofuran-2-yl]-methanone Step 1: 1-(2,4-Dihydroxy-phenyl)-2-methyl-propan-1-one Resorcinol (10.0 g, 91 mmol) and isobutyric acid (8.00 g, 1 eq.) were treated with $BF_3$-etherate (68 mL, 6 eq.) and heated for 1.5 h to 90° C. After cooling the reaction mixture was carefully poured onto 500 mL of 10% aq. NaOAc solution, twofold extracted with AcOEt, washed with water, dried over sodium sulfate, and evaporated to dryness to leave 18.5 g of the title compound as light brown oil.

MS (ISP): 180.9 $[M+H]^+$.

Step 2: 1-(2-Hydroxy-4-methoxy-phenyl)-2-methyl-propan-1-one

The above prepared 1-(2,4-dihydroxy-phenyl)-2-methyl-propan-1-one (1.13 g, 5.55 mmol, corrected for purity) was dissolved in 22 mL of acetonitrile and treated successively at 0° C. with iodomethane (0.36 mL, 1.05 eq.) and $Cs_2CO_3$ (1.998 g, 1.1 eq.), and the mixture then stirred over night at ambient temperature. Pouring onto crashed ice/$NH_4$Cl, twofold extraction with AcOEt, washing with water, drying over sodium sulfate, and evaporation of the solvents, followed by flash chromatography ($SiO_2$, hexane/AcOEt=95/5), delivered 0.740 g of the title compound as colorless oil.

MS (ISP): 195.1 $[M+H]^+$.

Step 3: (2-Isobutyryl-5-methoxy-phenoxy)-acetic acid ethyl ester

To a solution of the above prepared 1-(2-hydroxy-4-methoxy-phenyl)-2-methyl-propan-1-one (5.43 g, 28 mmol) in 56 mL acetonitrile were successively added $Cs_2CO_3$ (10.9 g, 1.2 eq.) and ethyl bromoacetate (3.25 mL, 1.05 eq.) and the mixture vigorously stirred at ambient temperature for 2.5 h. Pouring onto crashed ice/$NH_4$Cl, twofold extraction with AcOEt, washing with water, drying over sodium sulfate, and evaporation of the solvents left 8.01 g of the title product as light yellow oil, sufficiently pure to be used for the next step.

Step 4: 3-Isopropyl-6-methoxy-benzofuran-2-carboxylic acid ethyl ester

The above prepared (2-isobutyryl-5-methoxy-phenoxy)-acetic acid ethyl ester (8.01 g, 28 mmol) was dissolved in 70 mL of dimethoxyethane and treated at 0° C. with KOtBu (1.25 g, 0.4 eq.). After 150 Min., the reaction mixture was poured onto crashed ice/HCl, twofold extracted with AcOEt, washed with water, dried over sodium sulfate, and evaporated to dryness to leave 7.19 g of crude product which was processed as follows:

8 mL of conc. sulfuric acid was added at 0° C. and then the mixture kept for 30 Min. at ambient temperature. 100 mL of $CH_2Cl_2$ was added and the acid neutralized with an excess of $NaHCO_3$. Filtration, generously rinsing with $CH_2Cl_2$, evaporation of the solvents, and ensuing flash chromatography (SiO$_2$, hexane/AcOEt=95/5) gave finally 2.52 g of the title compound as light yellow oil.

Step 5: 6-Hydroxy-3-isopropyl-benzofuran-2-carboxylic acid ethyl ester

The above prepared 3-isopropyl-6-methoxy-benzofuran-2-carboxylic acid ethyl ester (2.52 g, 10 mmol) was dissolved in 65 mL of CH$_2$Cl$_2$, cooled to 0° C., and treated with BBr$_3$ (19.2 mL of 1M solution in CH$_2$Cl$_2$, 2 eq.). After 1 h at 0° C. and one additional at ambient temperature, the reaction mixture was carefully poured onto crashed ice, twofold extracted with AcOEt, washed with water, dried over sodium sulfate, and evaporated to dryness. Flash chromatography (SiO$_2$, hexane/AcOEt=8/2) afforded 0.930 g of the title compound as purple crystals.

MS (ISP): 247.1 [M−H]$^-$.

Step 6: 3-Isopropyl-6-(1-isopropyl-piperidin-4-yloxy)-benzofuran-2-carboxylic acid ethyl ester The above prepared 6-hydroxy-3-isopropyl-benzofuran-2-carboxylic acid ethyl ester (0.400 g, 1.61 mmol) was dissolved in 8 mL of THF and treated successively at 0° C. with 1-isopropyl-piperidin-4-ol (0.461 g, 2 eq.), triphenylphosphine (0.845 g, 2 eq.) and DIAD (0.630 mL, 2 eq.), and the mixture then kept at ambient temperature for another 1 h. Pouring onto crashed ice, twofold extraction with AcOEt, washing with water, drying over sodium sulfate, and evaporation of the solvents, followed by flash chromatography (SiO$_2$, NEt$_3$/AcOEt=5/95), yielded 0.720 g of the title compound as light yellow oil, contaminated with tiny amounts of reduced DIAD.

MS (ISP): 374.4 [M+H]$^+$.

Step 7: 3-Isopropyl-6-(1-isopropyl-piperidin-4-yloxy)-benzofuran-2-carboxylic acid The above prepared 3-isopropyl-6-(1-isopropyl-piperidin-4-yloxy)-benzofuran-2-carboxylic acid ethyl ester (0.720 g, 1.54 mmol, corrected for purity) was dissolved in 4 mL of THF/ethanol=1/1 and treated with 0.771 mL of aq. NaOH (3M, 1.5 eq.). The mixture was stirred for 3 h at ambient temperature and was then neutralized by adding 1.16 mL of 2M HCl (1.5 eq.). Careful evaporation of all solvents and drying afforded then 0.800 g of the title compound as light yellow foam contaminated with innocouos inorganic salts.

MS (ISP): 344.4 [M−H]$^-$.

Step 8: (4,4-Difluoro-piperidin-1-yl)-[3-isopropyl-6-(1-isopropyl-piperidinyloxy)-benzofuran-2-yl]-methanone In a flask were mixed together the above prepared 3-isopropyl-6-(1-isopropyl-piperidin-4-yloxy)-benzofuran-2-carboxylic acid (0.200 g, 0.386 mmol, corrected for purity), 4,4-difluoropiperidine hydrochloride (0.056 g, 1.2 eq.), (benzotriazol-1-yloxy)-tris-(dimethylamino)phosphonium hexafluorophosphate (0.153 g, 1.2 eq.) and 2.4 eq. of N-ethyldiisopropylamine (0.157 mL) in 3 mL of abs. THF and allowed to react during one night at ambient temperature. Pouring onto crashed ice/AcOEt/NH$_4$Cl-solution, twofold extraction with AcOEt, washing with water, drying over sodium sulfate, and evaporation of the solvents, followed by flash chromatography (SiO$_2$, CH$_2$Cl$_2$/MeOH=93/7) produced 0.063 g of the title compound as colorless gum.

MS (ISP): 449.3 [M+H]$^+$.

Example 9

4-[5-(1-Isopropyl-piperidin-4-yloxy)-benzo[b]thiophene-2-carbonyl]-piperazine-1-carboxylic acid tert-butyl ester The title compound was prepared in analogy to example 6, but using in step 5 piperazine-1-carboxylic acid tert-butyl ester instead of 4,4-difluoropiperidine, as light yellow solid.

MS (ISP): 488.2 [M+H]$^+$.

Example 10

(1,1-Dioxo-$_1\lambda$6thiomorpholin-4-yl)-[5-(1-isopropyl-piperidin-4-yloxy)-benzo[b]thiophen-2-yl]-methanone The title compound was prepared in analogy to example 6, but using in step 5 thiomorpholine 1,1-dioxide instead of 4,4-difluoropiperidine, as light yellow solid.

MS (ISP): 437.1 [M+H]$^+$.

Example 11

(1,1-Dioxo-$_1\lambda$6thiomorpholin-4-yl)-[5-(1-isopropyl-piperidin-4-yloxy)-6-methyl-benzofuran-2-yl]-methanone Step 1: 2,5-Dimethoxy-4-methyl-benzaldehyde To a solution of 2,5-dimethoxytoluene (4.66 g, 30.6 mmol) in 60 mL of N-methyl-N-phenyl-formamide was added at 0° C. POCl$_3$ (8.41 mL, 3 eq.), and the mixture was heated for 60 Min. to 80° C. After cooling, the reaction mixture was poured onto crashed ice, twofold extracted with AcOEt, washed with water, dried over sodium sulfate, and evaporated to dryness. Flash chromatography (SiO$_2$, hexane/AcOEt=9/1) afforded 4.153 g of the title compound as off-white solid.

MS (ISP): 181.3 [M+H]$^+$.

Step 2: 2-Hydroxy-5-methoxy-4-methyl-benzaldehyde

The above prepared 2,5-Dimethoxy-4-methyl-benzaldehyde (4.153 g, 23 mmol) was dissolved in 115 mL of acetonitrile and treated successively with sodium iodide (5.18 g, 1.5 eq.) and AlCl$_3$ (3.07 g, 1.0 eq.), and the mixture kept at 80° C. for 1 h. Cooling, pouring onto crashed ice, twofold extraction with AcOEt, washing with water, drying over sodium sulfate, and evaporation of the solvents, followed by flash chromatography (SiO$_2$, hexane/AcOEt=9/1), gave 3.80 g of the title compound as off-white solid.

MS (ISP): 165.4 [M−H]$^-$.

The remaining steps were performed as described in Example 1, step 1-6, to give (1,1-Dioxo-$_1\lambda$6thiomorpholin-4-yl)-[5-(1-isopropyl-piperidin-4-yloxy)-6-methyl-benzofuran-2-yl]-methanone as white solid.

MS (ISP): 435.4 [M+H]$^+$.

Example 12

((cis)-2,6-Dimethyl-morpholin-4-yl)-[5-(1-isopropyl-piperidin-4-yloxy)-6-methyl-benzofuran-2-yl]-methanone The title compound was prepared in analogy to example 11, but using in the final step (cis)-2,6-dimethyl-morpholine instead of thiomorpholine 1,1-dioxide, as yellow oil.

MS (ISP): 415.5 [M+H]$^+$.

Example 13

(4,4-Difluoro-piperidin-1-yl)-[5-(1-isopropyl-piperidin-4-yloxy)-6-methyl-benzofuran-2-yl]-methanone This compound was prepared in analogy to example 11, but using in the final step 4,4-difluoropiperidine instead of thiomorpholine 1,1-dioxide, as yellow oil.
MS (ISP): 421.2 [M+H]$^+$.

Example 14

1-{4-[5-(1-Isopropyl-piperidin-4-yloxy)-6-methyl-benzofuran-2-carbonyl]-piperazin-1-yl}-ethanone The title compound was prepared in analogy to example 11, but using in the final step 1-piperazin-1-yl-ethanone instead of thiomorpholine 1,1-dioxide, as off-white solid.
MS (ISP): 428.3 [M+H]$^+$.

Example 15

4-[5-(1-Isopropyl-piperidin-4-yloxy)-6-methyl-benzofuran-2-carbonyl]-piperazine-1-carboxylic acid methyl ester The title compound was prepared in analogy to example 11, but using in the final step piperazine-1-carboxylic acid methyl ester instead of thiomorpholine 1,1-dioxide, as white solid.
MS (ISP): 444.2 [M+H]$^+$.

Example 16

(4,4-Difluoro-piperidin-1-yl)-[6-(1-isopropyl-piperidin-4-yloxy)benzofuran-2-yl]-methanone The title compound was prepared in analogy to example 4, hut starting the whole reaction sequence with 2-hydroxy-4-methoxy-benzaldehyde instead of 2-hydroxy-5-methoxy-benzaldehyde, as white crystals.
MS (ISP): 407.3 [M+H]$^+$.

Example 17

(4,4-Difluoro-piperidin-1-yl)-[6-(1-isopropyl-piperidin-4-yloxy)-3-phenyl-benzofuran-2-yl]-methanone Step 1: (2,4-Dihydroxy-phenyl)-phenyl-methanone
Resorcinol (1.10 g, 10.0 mmol) and benzoic acid (1.22 g, 1.01 eq.) were treated with BF$_3$-etherate (7.55 mL, 6 eq.) and heated for 2 h to 95° C. After cooling the reaction mixture was carefully poured onto 500 mL of 10% aq. NaOAc solution, twofold extracted with AcOEt, washed with water, dried over sodium sulfate, and evaporated to dryness. Flash chromatography (SiO$_2$, heptane/AcOEt=8/2), followed by direct crystallization after reducing the volume, afforded 0.994 g of the title compound as off-white crystals.
MS (ISP): 212.9 [M–H]$^-$.

Step 2: (2-Hydroxy-4-methoxy-phenyl)-phenyl-methanone
The above prepared (2,4-dihydroxy-phenyl)-phenyl-methanone (0.775 g, 3.62 mmol) was dissolved in 15 mL of acetonitrile and treated successively at 0° C. with Cs$_2$CO$_3$ (1.297 g, 1.1 eq.) and iodomethane (0.242 mL, 1.08 eq.), and the mixture was then stirred over night at ambient temperature. Pouring onto crashed ice/NH$_4$Cl, twofold extraction with AcOEt, washing with water, drying over sodium sulfate, and evaporation of the solvents, followed by flash chromatography (SiO$_2$, heptane/AcOEt=9/1), delivered 0.681 g of the title compound as off-white oil.
MS (ISP): 226.9 [M–H]$^-$.

The remaining steps were performed as described in Example 8, step 3-8, to give (4,4-Difluoro-piperidin-1-yl)-[6-(1-isopropyl-piperidin-4-yloxy)-3-phenyl-benzofuran-2-yl]-methanone as off-white foam.
MS (ISP): 483.3 [M+H]$^+$.

Example 18

4-[6-(1-Isopropyl-piperidin-4-yloxy)-benzofuran-2-carbonyl]-piperazine-1-carboxylic acid methyl ester The title compound was prepared in analogy to example 16, but using in the final step piperazine-1-carboxylic acid methyl ester instead of 4,4-difluoropiperidine, as colorless gum.
MS (ISP): 430.4 [M+H]$^+$.

Example 19

[6-(1-Cyclobutyl-piperidin-4-yloxy)-benzo[b]thiophen-2-yl]-(4,4-difluoro-piperidin-1-yl)-methanone Step 1: 4-(2-Ethoxycarbonyl-benzo[b]thiophen-6-yloxy)-piperidine-1-carboxylic acid tert-butyl ester
The above prepared 6-hydroxy-benzo[b]thiophene-2-carboxylic acid ethyl ester (0.206 g, 0.927 mmol, see example 7, step 1 and 2) was dissolved in 5 mL of THF and treated successively at –10° C. with 4-hydroxy-piperidine-1-carboxylic acid tert-butyl ester (0.261 g, 1.4 eq.), triphenylphosphine (0.340 g, 1.4 eq.) and DIAD (0.255 mL, 2 eq.), and the mixture then kept at ambient temperature over night. Pouring onto crashed ice, twofold extraction with AcOEt, washing with water and brine, drying over magnesium sulfate, and evaporation of the solvents, followed by flash chromatography (SiO$_2$, hexane AcOEt=85/15), yielded 0.355 g of the title compound as colorless gum.
MS (ISP): 406.5 [M+H]$^+$.

Step 2: 6-(1-Cyclobutyl-piperidin-4-yloxy)-benzo[b]thiophene-2-carboxylic acid ethyl ester
The above prepared 4-(2-ethoxycarbonyl-benzo[b]thiophen-6-yloxy)-piperidine-1-carboxylic acid tert-butyl ester (0.330 g, 0.814 mmol) was dissolved in 2 mL of dioxane and treated with HCl (4.1 mL of 4N [dioxane], 20 eq.) and the mixture kept at ambient temperature for 2 h. Reducing the volume, adding heptane, and direct crystallization produced 0.261 g of 6-(piperidin-4-yloxy)-benzo[b]thiophene-2-carboxylic acid ethyl ester as hydrochloride as white crystals, which was further processed as follows:
It was dissolved in 2.4 mL of CH$_2$Cl$_2$ and treated successively with cyclobutanone (0.056 g, 2 eq.), acetic acid (0.046 mL, 2 eq.) and sodium triacetoxyborohydride (0.170 g, 2 eq.), and the mixture then kept at ambient temperature for 2 h. Pouring onto crashed ice, twofold extraction with AcOEt, washing with water and brine, drying over magnesium sulfate, and evaporation of the solvents, followed by trituration in AcOEt/hexane, yielded 0.139 g of the title compound as white crystals.
MS (ISP): 360.2 [M+H]$^+$.

The remaining steps were performed as described in Example 7, step 4 and 5, to give [6-(1-Cyclobutyl-piperidin- 4-yloxy)-benzo[b]thiophen-2-yl]-(4,4-difluoro-piperidin-1-yl)-methanone as off-white crystals.

MS (ISP): 435.2 [M+H]$^+$.

Example 20

[6-(1-Cyclobutyl-piperidin-4-yloxy)-benzo[b]thiophen-2-yl]-((cis)-2,6-dimethyl-morpholin-4-yl)-methanone This compound was prepared in analogy to example 19, but using in the final step (cis)-2,6-dimethyl-morpholine instead of 4,4-difluoropiperidine, as white foam.

MS (ISP): 429.3 [M+H]$^+$.

Example 21

[6-(1-Cyclobutyl-piperidin-4-yloxy)-benzofuran-2-yl]-(4,4-difluoro-piperidin-1-yl)-methanone This compound was prepared in analogy to example 19, but using in the first step 6-hydroxy-benzofuran-2-carboxylic acid ethyl ester instead of 6-hydroxy-benzo[b]thiophene-2-carboxylic acid ethyl ester, as light brown solid.

MS (ISP): 419.1 [M+H]$^+$.

Example 22

[6-(1-Cyclobutyl-piperidin-4-yloxy)-benzofuran-2-yl]-((cis)-2,6-dimethyl-morpholin-4-yl)-methanone This compound was prepared in analogy to example 21, but using in the final step (cis)-2,6-dimethyl-morpholine instead of 4,4-difluoropiperidine, as light brown gum.

MS (ISP): 413.3 [M+H]$^+$.

Example 23

[5-(1-Cyclobutyl-piperidin-4-yloxy)-6-methyl-benzofuran-2-yl]-(4,4-difluoro-piperidin-1-yl)-methanone The title compound was prepared in analogy to example 21, but using in the first step 5-hydroxy-6-methyl-benzofuran-2-carboxylic acid ethyl ester (see example 11) instead of 6-hydroxy-benzofuran-2-carboxylic acid ethyl ester, as light brown solid.

MS (ISP): 433.3 [M+H]$^+$.

Example 24

[5-(1-Cyclobutyl-piperidin-4-yloxy)-6-methyl-benzofuran-2-yl]-(1,1-dioxo-$_1\lambda$6thiomorpholin-4-yl)-methanone This compound was prepared in analogy to example 23, but using in the final step thiomorpholine 1,1-dioxide instead of 4,4-difluoropiperidine, as white foam.

MS (ISP): 447.0 [M+H]$^+$.

Example 25

[5-(1-Cyclobutyl-piperidin-4-yloxy)-6-methyl-benzofuran-2-yl]-((cis)-2,6-dimethyl-morpholin-4-yl)-methanone The title compound was prepared in analogy to example 23, but using in the final step (cis)-2,6-dimethyl-morpholine instead of 4,4-difluoropiperidine, as off-white solid.

MS (ISP): 427.3 [M+H]$^+$.

Example 26

4-[5-(1-Cyclobutyl-piperidin-4-yloxy)-6-methyl-benzofuran-2-carbonyl]-piperazine-1-carboxylic acid methyl ester This compound was prepared in analogy to example 23, but using in the final step piperazine-1-carboxylic acid methyl ester instead of 4,4-difluoropiperidine, as white solid.

MS (ISP): 456.3 [M+H]$^+$.

Example 27

[6-(1-Cyclobutyl-piperidin-4-yloxy)-benzofuran-2-yl]-(1,1-dioxo-$_1\lambda$6thiomorpholin-4-yl)-methanone This compound was prepared in analogy to example 21, but using in the final step thiomorpholine 1,1-dioxide instead of 4,4-difluoropiperidine, as colorless gum.

MS (ISP): 433.2 [M+H]$^+$.

Example 28

[6-Chloro-5-(1-isopropyl-piperidin-4-yloxy)-benzofuran-2-yl]-(4,4-difluoro-piperidin-1-yl)-methanone Step 1: 3-Chloro-4-methoxy-phenol 3-Chloro-4-methoxybenzaldehyde (2.50 g, 15.0 mmol) was dissolved in 30 mL of CH$_2$Cl$_2$, treated with 3-chloro-perbenzoic acid (4.84 g, 70%, 1.4 eq.), and then kept for 3.5 h at ambient temperature. Pouring onto crashed ice/pyrosulfite-solution, twofold extraction with AcOEt, washing with Na$_2$CO$_3$-solution, drying over sodium sulfate, and evaporation of the solvents left 2.89 g of the intermediate formiate which was hydrolysed by stirring for 20 Min. in 25 mL of MeOH containing 2.113 g of K$_2$CO$_3$. Standard extractive work-up delivered then 2.60 g of the title compound sufficiently pure for the next step.

Step 2: 4-Chloro-2-hydroxy-5-methoxy-benzaldehyde

The above prepared 3-chloro-4-methoxy-phenol (2.379 g, 13.5 mmol, corrected for purity) was dissolved in 21 mL of trifluoroacetic acid and treated with hexamethylene tetramine (2.313 g, 1.25 eq.), and the mixture was then stirred at 85° C. over night. Cooling, pouring onto crashed ice, twofold extraction with AcOEt, washing with water, drying over sodium sulfate, and evaporation of the solvents, followed by flash chromatography (SiO$_2$, heptane/AcOiPr=82/18), followed by crystallization from heptane/AcOEt, produced finally 1.030 g of the title compound as yellow crystals.

MS (ISP): 185.1 [M+H]$^+$.

Example 29

[6-Chloro-5-(1-isopropyl-piperidin-4-yloxy)-benzo-furan-2-yl]-((cis)-2,6-dimethyl-morpholin-4-yl)-methanone The title compound was prepared in analogy to example 28, but using in the final step (cis)-2,6-dimethyl-morpholine instead of 4,4-difluoropiperidine, as light yellow viscous oil.

MS (ISP): 435.2 [M+H]$^+$.

Example 30

[6-Chloro-5-(1-isopropyl-piperidin-4-yloxy)-benzo-furan-2-yl]-(1,1-dioxo-$_1\lambda$6thiomorpholin-4-yl)-methanone This compound was prepared in analogy to example 28, but using in the final step thiomorpholine 1,1-dioxide instead of 4,4-difluoropiperidine, as white solid.

MS (ISP): 455.3 [M+H]$^+$.

Example 31

[5-(1-Cyclobutyl-piperidin-4-yloxy)benzo[b]thiophen-2-yl]-(4,4-difluoro-piperidin-1-yl)-methanone The title compound was prepared in analogy to example 19, but using in the first step 5-hydroxy-benzo[b]thiophene-2-carboxylic acid methyl ester instead of 6-hydroxy-benzo[b]thiophene-2-carboxylic acid ethyl ester, as white solid.

MS (ISP): 435.2 [M+H]$^+$.

Example 32

[5-(1-Cyclobutyl-piperidin-4-yloxy)-benzo[b]thiophen-2-yl]-((cis)-2,6-dimethyl-morpholin-4-yl)-methanone This compound was prepared in analogy to example 31, but using in the final step (cis)-2,6-dimethyl-morpholine instead of 4,4-difluoropiperidine, as colorless foam.

MS (ISP): 429.3 [M+H]$^+$.

Example 33

4-[5-(1-Isopropyl-piperidin-4-yloxy)-benzo[b]thiophene-2-carbonyl]-piperazine-1-carboxylic acid methyl ester The compound was prepared in analogy to example 9, but using in the final step piperazine-1-carboxylic acid methyl ester instead of piperazine-1-carboxylic acid tert-butyl ester, as white solid.

MS (ISP): 446.3 [M+H]$^+$.

Example 34

4-[6-(1-Isopropyl-piperidin-4-yloxy)-3-phenyl-benzofuran-2-carbonyl]-piperazine-1-carboxylic acid methyl ester This compound was prepared in analogy to example 17, but using in the final step piperazine-1-carboxylic acid methyl ester instead of 4,4-difluoropiperidine, as colorless oil.

MS (ISP): 506.2 [M+H]$^+$.

Example 35

((cis)-2,6-Dimethyl-morpholin-4-yl)-[6-(1-isopropyl-piperidin-4-yloxy)-3-phenyl-benzofuran-2-yl]-methanone The compound was prepared in analogy to example 17, but using in the final step (cis)-2,6-dimethyl-morpholine instead of 4,4-difluoropiperidine, as colorless oil.

MS (ISP): 477.1 [M+H]$^+$.

Example 36

[5-Chloro-3-isopropyl-6-(1-isopropyl-piperidin-4-yloxy)-benzofuran-2-yl]-(4,4-difluoro-piperidin-1-yl)-methanone Step 1: 5-Chloro-2-hydroxy-4-methoxy-benzaldehyde 2-Hydroxy-4-methoxy-benzaldehyde (0.974 g, 6.40 mmol) was dissolved in 10 mL of acetonitrile and treated with N-chlorosuccinimide (0.983 g, 1.15 eq.) and ammonium nitrate (0.102 g, 0.20 eq.), and the mixture was warmed to 70° C. for roughly 5 h. Evaporation of the solvent, followed by flash chromatography (SiO$_2$, heptane/AcOEt=85/15), and direct crystallization from heptane/AcOEt, produced then 0.259 g of the title compound as white crystals.

MS (ISP): 185.1 [M–H]$^-$.

Step 2: 4-Chloro-2-(1-hydroxy-2-methyl-propyl)-5-methoxy-phenol

The above prepared 5-chloro-2-hydroxy-4-methoxy-benzaldehyde (0.845 g, 4.53 mmol) was dissolved in 10 mL of abs. THF and treated at –15° C. with iPrMgCl (4.98 mL of 2M [THF], 2.2 eq.) and the mixture kept at this temperature for 0.5 h. Careful pouring onto crashed ice/NH$_4$Cl, twofold extraction with AcOEt, washing with water, drying over sodium sulfate, and evaporation of the solvents left 1.090 g of the title compound as light brown oil, almost perfectly pure according to TLC and NMR.

MS (ISP): 229.1 [M–H]$^-$.

Step 3: [4-Chloro-2-(1-hydroxy-2-methyl-propyl)-5-methoxy-phenoxy]-acetic acid ethyl ester To a solution of the above prepared 4-chloro-2-(1-hydroxy-2-methyl-propyl)-5-methoxy-phenol (1.080 g, 4.68 mmol) in 15 mL acetonitrile were successively added Cs$_2$CO$_3$ (1.98 g, 1.3 eq.) and ethyl bromoacetate (0.596 mL, 1.15 eq.) and the mixture vigorously stirred at ambient temperature over night. Pouring onto crashed ice/NH$_4$Cl, twofold extraction with AcOEt, washing with water, drying over sodium sulfate, and evaporation of the solvents left 1.57 g of the title compound as light brown oil, used directly for the next step.

MS (ISP): 299.3 [M–H$_2$O+H]$^+$.

Step 4: (4-Chloro-2-isobutyryl-5-methoxy-phenoxy)-acetic acid ethyl ester

The above prepared [4-chloro-2-(1-hydroxy-2-methyl-propyl)-5-methoxy-phenoxy]-acetic acid ethyl ester (1.56 g, 4.92 mmol) was dissolved in 50 mL of $CH_2Cl_2$, treated with $MnO_2$ (12.84 g, 30 eq.), and the reaction mixture vigorously stirred over night at 35-40° C. Cooling, filtration over a pad of Celite, copiously rinsing, and evaporation of the solvent, followed by flash chromatography ($SiO_2$, heptane/AcOEt=72/28) and direct crystallization afforded 0.887 g of the title compound as off-white crystals.

MS (ISP): 315.1 $[M+H]^+$.

The remaining steps were performed as described in Example 8, step 4-8, to give [5-Chloro-3-isopropyl-6-(1-isopropyl-piperidin-4-yloxy)-benzofuran-2-yl]-(4,4-difluoro-piperidin-1-yl)-methanone as off-white oil.

MS (ISP): 483.3 $[M+H]^+$.

Example 37

((cis)-2,6-Dimethyl-morpholin-4-yl)-[6-(1-isopropyl-piperidin-4-yloxy)-5-methyl-3-benzyl-benzofuran-2-yl]-methanone The compound was prepared in analogy to example 35, but starting the reaction sequence with 4-methyl-resorcinol instead of resorcinol, as white foam.

MS (ISP): 491.4 $[M+H]^+$.

Example 38

4-[6-(1-Isopropyl-piperidin-4-yloxy)-5-methyl-3-phenyl-benzofuran-2-carbonyl]-piperazine-1-carboxylic acid methyl ester The title compound was prepared in analogy to example 37, but using in the final step piperazine-1-carboxylic acid methyl ester instead of (cis)-2,6-dimethyl-morpholine, as white foam.

MS (ISP): 520.3 $[M+H]^+$.

Example 39

(1,1-Dioxo-$_1\lambda$6thiomorpholin-4-yl)-[6-(1-isopropyl-piperidin-4-yloxy)-5-methyl-3-phenyl benzofuran-2-yl]-methanone The title compound was prepared in analogy to example 37, but using in the final step thiomorpholine 1,1-dioxide instead of (cis)-2,6-dimethyl-morpholine, as white solid.

MS (ISP): 511.4 $[M+H]^+$.

Example 40

(4,4-Difluoro-piperidin-1-yl)-[6-(1-isopropyl-piperidin-4-yloxy)-5-methyl-3-phenyl-benzofuran-2-yl]-methanone The title compound was prepared in analogy to example 37, but using in the final step 4,4-difluoropiperidine instead of (cis)-2,6-dimethyl-morpholine, as white foam.

MS (ISP): 497.2 $[M+H]^+$.

Example 41

[5-(1-Cyclobutyl-piperidin-4-yloxy)-benzofuran-2-yl]-((cis)-2,6-methyl-morpholin-4-yl)-methanone This compound was prepared in analogy to example 32, but using in the first step 5-hydroxy-benzofuran-2-carboxylic acid ethyl ester instead of 5-hydroxy-benzo[b]thiophene-2-carboxylic acid methyl ester, as light yellow gum.

MS (ISP): 413.2 $[M+H]^+$.

Example 42

[5-(1-Cyclobutyl-piperidin-4-yloxy)-benzofuran-2-yl]-(4,4-difluoro-piperidin-1-yl)-methanone The title compound was prepared in analogy to example 41, but using in the final step 4,4-difluoropiperidine instead of (cis)-2,6-dimethyl-morpholine, as off-white crystals.

MS (ISP): 419.2 $[M+H]^+$.

Example 43

[5-(1-Cyclobutyl-piperidin-4-yloxy)-benzofuran-2-yl]-(1,1-dioxo-$_1\lambda$6thiomorpholin-4-yl)-methanone This compound was prepared in analogy to example 41, but using in the final step thiomorpholine 1,1-dioxide instead of (cis)-2,6-dimethyl-morpholine, as white crystals.

MS (ISP): 433.2 $[M+H]^+$.

Example 44

4-[5-(1-Cyclobutyl-piperidin-4-yloxy)-benzofuran-2-carbonyl]-piperazine-1-carboxylic acid methyl ester This compound was prepared in analogy to example 41, but using in the final step piperazine-1-carboxylic acid methyl ester instead of (cis)-2,6-dimethyl-morpholine, as light brown crystals.

MS (ISP): 442.4 $[M+H]^+$.

Example 45

4-[3-(4-Fluoro-phenyl)-6-(1-isopropyl-piperidin-4-yloxy)-benzofuran-2-carbonyl]-piperazine-1-carboxylic acid methyl ester Step 1: (2,4-Dimethoxy-phenyl)-(4-fluoro-phenyl)methanone 1,3-Dimethoxybenzene (5.00 g, 36.2 mmol) and $AlCl_3$ (5.79 g, 1.2 eq.) were dissolved in 360 ml of $CH_2Cl_2$ and cooled down to 0° C. 4-Fluoro-benzoyl chloride (4.34 mL, 1.0 eq.) was slowly added via dropping funnel and the mixture allowed to react for another h at ambient temperature. Pouring onto crashed ice, twofold extraction with AcOEt, washing with water and brine, drying over sodium sulfate, and evaporation of the solvents, followed by short flash chromatography ($SiO_2$, hexane/AcOEt 8/2), yielded 7.75 g of the title compound as white solid.

MS (ISP): 261.0 $[M+H]^+$.

Step 2: (4-Fluoro-phenyl)-(2-hydroxy-4-methoxy-phenyl)-methanone

The above prepared (2,4-Dimethoxy-phenyl)-(4-fluoro-phenyl)-methanone (7.75 g, 29.8 mmol) was dissolved in 150 mL of acetonitrile and treated successively with sodium iodide (6.70 g, 1.5 eq.) and AlCl₃ (3.97 g, 1.0 eq.), and the mixture kept at 80° C. for 1.5 h. Cooling, pouring onto crashed ice, twofold extraction with AcOEt, washing with water and brine, drying over sodium sulfate, and evaporation of the solvents, followed by a short flash chromatography (SiO₂, hexane/AcOEt=9/1), gave 6.49 g of the title compound as yellow solid.

MS (ISP): 245.1 [M–H]⁻.

The remaining steps were performed as described in Example 8, step 3-8, to give 4-[3-(4-Fluoro-phenyl)-6-(1-isopropyl-piperidin-4-yloxy)-benzofuran-2-carbonyl]-piperazine-1-carboxylic acid methyl ester as white foam.

MS (ISP): 524.3 [M+H]⁺.

Example 46

((cis)-2,6-Dimethyl-morpholin-4-yl)-[3-(4-fluoro-phenyl)-6-(1-isopropyl-piperidin-4-yloxy)-benzofuran-2-yl]-methanone This compound was prepared in analogy to example 45, but using in the final step (cis)-2,6-dimethyl-morpholine instead of piperazine-1-carboxylic acid methyl ester, as white foam.
MS (ISP): 495.3 [M+H]⁺.

Example 47

(1,1-Dioxo-1λ6thiomorpholin-4-yl)-[3-(4-fluoro-phenyl)-6-(1-isopropyl-piperidin-4-yloxy)-benzofuran-2-yl]-methanone The compound was prepared in analogy to example 45, but using in the final step thiomorpholine 1,1-dioxide instead of piperazine-1-carboxylic acid methyl ester, as white solid.
MS ([SP): 515.3 [M+H]⁺.

Example 48

(4,4-Difluoro-piperidin-1-yl)-[3-(4-fluoro-phenyl)-6-(1-isopropyl-piperidin-4-yloxy)-benzofuran-2-yl]-methanone This compound was prepared in analogy to example 45, but using in the final step 4,4-difluoropiperidine instead of piperazine-1-carboxylic acid methyl ester, as white foam.
MS (ISP): 501.1 [M+H]⁺.

Example 49

(4,4-Difluoro-piperidin-1-yl)-[3-isopropyl-6-(1-isopropyl-piperidin-4-yloxy)-5-methyl-benzofuran-2-yl]-methanone Step 1: 2,4-Dimethoxy-5-methyl-benzaldehyde To a solution of 2,4-dimethoxytoluene (5.50 g, 36.1 mmol) in 55 mL of N-methyl-N-phenyl-formamide was added at 0° C. POCl₃ (10.9 mL, 3 eq.), and the mixture was heated for 60 Min. to 80° C. After cooling, the reaction mixture was poured onto crashed ice, the precipitate filtered and washed twice with water/MeOH=8/2 to leave after drying 5.40 g of the title product as light yellow crystals.

MS (ISP): 181.0 [M+H]⁺.

Step 2: 2-Hydroxy-4-methoxy-5-methyl-benzaldehyde

The above prepared 2,4-Dimethoxy-5-methyl-benzaldehyde (5.40 g, 30 mmol) was dissolved in 150 mL of acetonitrile and treated successively with sodium iodide (6.74 g, 1.5 eq.) and AlCl₃ (4.00 g, 1.0 eq.), and the mixture kept at 80° C. for 1 h. Cooling, pouring onto crashed ice, twofold extraction with AcOEt, washing with water and brine, drying over magnesium sulfate, and evaporation of the solvents, followed by flash chromatography (SiO₂, hexane/AcOEt=9/1), delivered 4.23 g of the title compound as light brown crystals.

MS (ISP): 165.1 [M–H]⁻.

Step 3: 2-(1-Hydroxy-2-methyl-propyl)-5-methoxy-4-methyl-phenol

The above prepared 2-hydroxy-4-methoxy-5-methyl-benzaldehyde (1.97 g, 11.86 mmol) was dissolved in 30 mL of abs. THF and treated at –15° C. with iPrMgCl (14.8 mL of 2M [THF], 2.5 eq.) and the mixture kept at this temperature for 0.5 h. Careful pouring onto crashed ice/NH₄Cl, twofold extraction with AcOEt, washing with water and brine, drying over magnesium sulfate, and evaporation of the solvents left 2.45 g of the title compound as white crystals, almost perfectly pure according to TLC and NMR.

MS (ISP): 209.2 [M–H]⁻.

Step 4: [2-(1-Hydroxy-2-methyl-propyl)-5-methoxy-4-methyl-phenoxy]-acetic acid ethyl ester To a solution of the above prepared 2-(1-hydroxy-2-methyl-propyl)-5-methoxy-4-methyl-phenol (2.45 g, 11.65 mmol) in 22 mL acetonitrile were successively added Cs₂CO₃ (4.56 g, 1.2 eq.) and ethyl bromoacetate (1.35 mL, 1.05 eq.) and the mixture vigorously stirred at ambient temperature for 3 h. Pouring onto crashed ice/NH₄Cl, twofold extraction with AcOEt, washing with water and brine, drying over magnesium sulfate, and evaporation of the solvents, followed by flash chromatography (SiO₂, hexane/AcOEt=8/2), gave 3.34 g of the title compound as colorless oil.

MS (ISP): 279.0 [M–H₂O+H]⁺.

Step 5: (2-Isobutyryl-5-methoxy-4-methyl-phenoxy)-acetic acid ethyl ester

To a solution of the above prepared [2-(1-hydroxy-2-methyl-propyl)-5-methoxy-4-methyl-phenoxy]-acetic acid ethyl (1.20 g, 4.05 mmol) in 40 mL of CH₂Cl₂ were successively added 4-methyl-morpholine N-oxide monohydrate (0.712 g, 1.5 eq.) and 8 g of powdered molecular sieves (4 Å) and the mixture vigorously stirred at ambient temperature for 10 Min. Tetrapropylammonium perrhutenate (0.071 g, 0.05 eq.) was then added as solid and stirring continued for 30 Min. Filtration over a pad of Celite, generously rinsing, and evaporation of the solvent, followed by flash chromatography (SiO₂, hexane/AcOEt=8/2), delivered 1.15 g of the title compound as white crystals.

MS (ISP): 295.1 [M+H]⁺.

Step 6: 3-Hydroxy-3-isopropyl-6-methoxy-5-methyl-2,3-dihydro-benzofuran-2-carboxylic acid ethyl ester The above prepared (2-isobutyryl-5-methoxy-4-methyl-phenoxy)-acetic acid ethyl ester (1.14 g, 3.87 mmol) was dissolved in 7.5 mL of dimethoxyethane and treated at –15° C. with KOtBu (0.174 g, 0.4 eq.). After 15 Min., TLC indicated the absence of starting material. The reaction mixture was poured onto crashed ice/HCl, twofold extracted with AcOEt, washed with water, dried over magnesium sulfate, and evaporated to dryness to leave 1.12 g of crude product containing the title compound and already some benzofuran which was processed as follows:

Step 7: 3-Isopropyl-6-methoxy-5-methyl-benzofuran-2-carboxylic acid ethyl ester

The product of Step 6 was dissolved in 25 mL of CH₂Cl₂, cooled to 0° C., and treated with BBr₃ (18.0 mL of 1M solution in CH₂Cl₂, 3 eq.). After 2.5 h at 0° C., the reaction mixture was carefully poured onto crashed ice, twofold extracted with AcOEt, washed with water, dried over magnesium sulfate, and evaporated to dryness. Flash chromatography (SiO$_2$, hexane/AcOEt=8/2) yielded finally 1.006 g of the title compound as off-white crystals.

MS (ISP): 263.0 [M+H]$^+$.

The remaining steps were performed as alluded to in Example 40 to give (4,4-Difluoro-piperidin-1-yl)-[3-isopropyl-6-(1-isopropyl-piperidin-4-yloxy)-5-methyl-benzofuran-2-yl]-methanone as off-white crystals.

MS (ISP): 463.2 [M+H]$^+$.

Example 50

((cis)-2,6-Dimethyl-morpholin-4-yl)-[3-isopropyl-6-(1-isopropyl-piperidin-4-yloxy)-5-methyl-benzofuran-2-yl]-methanone The title compound was prepared in analogy to example 49, but using in the final step (cis)-2,6-dimethyl-morpholine instead of 4,4-difluoropiperidine, as white solid.

MS (ISP): 457.3 [M+H]$^+$.

Example 51

(1,1-Dioxo-$_1\lambda$6thiomorpholin-4-yl)-[3-isopropyl-6-(1-isopropyl-piperidin-4-yloxy)-5-methyl-benzofuran-2-yl]-methanone The compound was prepared in analogy to example 49, but using in the final step thiomorpholine 1,1-dioxide instead of 4,4-difluoropiperidine, as white crystals.

MS (ISP): 477.1 [M+H]$^+$.

Example 52

[5-Chloro-6-(1-isopropyl-piperidine-4-yloxy)-3-phenyl-benzofuran-2-yl]-(4,4-difluoro-piperidin-1-yl)-methanone Step 1: 4-Chloro-2-(hydroxy-phenyl-methyl)-5-methoxy-phenol The above prepared 5-chloro-2-hydroxy-4-methoxy-benzaldehyde (example 36, step 1, 1.050 g, 5.63 mmol) was dissolved in 15 mL of abs. THF and treated at −15° C. with PhMgBr (15.5 mL of 1M [THF], 2.7 eq.) and the mixture kept at this temperature for 0.5 h. Careful pouring onto crashed ice/NH$_4$Cl, twofold extraction with AcOEt, washing with water, drying over sodium sulfate, and evaporation of the solvents, followed by flash chromatography (SiO$_2$, hexane/AcOEt=7/3) yielded 1.39 g of the title compound as light brown oil.

MS (ISP): 263.0 [M−H]$^−$.

Step 2: [4-Chloro-2-(hydroxy-phenyl-methyl)-5-methoxy-phenoxy]-acetic acid ethyl ester To a solution of the above prepared 4-chloro-2-(hydroxy-phenyl-methyl)-5-methoxy-phenol (1.39 g, 5.25 mmol) in 15 mL acetonitrile were successively added Cs$_2$CO$_3$ (2.22 g, 1.3 eq.) and ethyl bromoacetate (0.67 mL 1.15 eq.) and the mixture vigorously stirred at ambient temperature over night. Pouring onto crashed ice/NH$_4$Cl, twofold extraction with AcOEt, washing with water, drying over sodium sulfate, and evaporation of the solvents left 1.91 g of the title compound as off-white gum, used directly for the next step.

MS (ISP): 333.0 [M−H$_2$O+H]$^+$.

Step 3: (2-Benzoyl-4-chloro-5-methoxy-phenoxy)-acetic acid ethyl ester

The above prepared [4-chloro-2-(hydroxy-phenyl-methyl)-5-methoxy-phenoxy]-acetic acid ethyl ester (1.91 g, 3.81 mmol, corrected for purity) was dissolved in 50 mL of CH$_2$Cl$_2$, treated with MnO$_2$ (8.28 g, 25 eq.), and the reaction mixture vigorously stirred over night. Filtration over a pad of Celite, carefully rinsing, and evaporation of the solvent, followed by flash chromatography (SiO$_2$, heptane/AcOEt=7/3) and crystallization from heptane/AcOEt gave 0.530 g of the title compound as white crystals.

MS (ISP): 349.4 [M+H]$^+$.

The remaining steps were performed as described in Example 49, step 6 and following, to give [5-Chloro-6-(1-isopropyl-piperidin-4-yloxy)-3-phenyl-benzofuran-2-yl]-(4,4-difluoro-piperidin-1-yl)-methanone as colorless oil.

MS (ISP): 517.5 [M+H]$^+$.

Example 53

4-[3-Isopropyl-6-(1-isopropyl-piperidin-4-yloxy)-5-methyl-benzofuran-2-carbonyl]-piperazine-1-carboxylic acid methyl ester This compound was prepared in analogy to example 49, but using in the final step piperazine-1-carboxylic acid methyl ester instead of 4,4-difluoropiperidine, as light yellow gum.

MS (ISP): 486.4 [M+H]$^+$.

Example 54

4-[5-Chloro-6-(1-isopropyl-piperidin-4-yloxy)-3-phenyl-benzofuran-2-carbonyl]-piperazine-1-carboxylic acid methyl ester This compound was prepared in analogy to example 52, but using in the final step piperazine-1-carboxylic acid methyl ester instead of 4,4-difluoropiperidine, as white crystals.

MS (ISP): 540.4 [M+H]$^+$.

Example 55

[6-(1-Cyclobutyl-piperidin-4-yloxy)-3-phenyl-benzofuran-2-yl]-(4,4-difluoro-piperidin-1-yl)-methanone The title compound was prepared in analogy to example 19, but using in the first step 6-hydroxy-3-phenyl-benzofuran-2-carboxylic acid ethyl ester instead of 6-hydroxy-benzo[b]thiophene-2-carboxylic acid ethyl ester, as white foam.

MS (ISP): 495.3 [M+H]$^+$.

Example 56

[6-(1-Cyclobutyl-piperidin-4-yloxy)-3-phenyl-benzofuran-2-yl]-(1,1-dioxo-$_1\lambda$6thiomorpholin-4-yl)-methanone This compound was prepared in analogy to example 55, but using in the final step thiomorpholine 1,1-dioxide instead of 4,4-difluoropiperidine, as white solid.

MS (ISP): 509.3 [M+H]$^+$.

Example 57

[6-(1-Cyclobutyl-piperidin-4-yloxy)-3-phenyl-benzofuran-2-yl]-((cis)-2,6-dimethyl-morpholin-4-yl)- methanone

This compound was prepared in analogy to example 55, but using in the final step (cis)-2,6-dimethyl-morpholine instead of 4,4-difluoropiperidine, as white foam.
MS (ISP): 489.3 [M+H]$^+$.

Example 58

[6-(1-Cyclobutyl-piperidin-4-yloxy)-3-isopropyl-5-methyl-benzofuran-2-yl]-(4,4-difluoro-piperidin-1-yl)-methanone This compound was prepared in analogy to example 19, but using in the first step 6-hydroxy-3-isopropyl-5-methyl-benzofuran-2-carboxylic acid ethyl ester instead of 6-hydroxy-benzo[b]thiophene-2-carboxylic acid ethyl ester, as white solid.
MS (ISP): 475.2 [M+H]$^+$.

Example 59

[6-(1-Cyclobutyl-piperidin-4-yloxy)-3-isopropyl-5-methyl-benzofuran-2-yl]-((cis)-2,6-dimethyl-morpholin-4-yl)-methanone The title compound was prepared in analogy to example 58, but using in the final step (cis)-2,6-dimethyl-morpholine instead of 4,4-difluoropiperidine, as white foam.
MS (ISP): 496.4 [M+H]$^+$.

Example 60

[6-(1-Cyclobutyl-piperidin-4-yloxy)-3-isopropyl-5-methyl-benzofuran-2-yl]-(1,1-dioxo-$_1\lambda$6thiomorpholin-4-yl)-methanone This compound was prepared in analogy to example 58, but using in the final step thiomorpholine 1,1-dioxide instead of 4,4-difluoropiperidine, as white crystals.
MS (ISP): 489.3 [M+H]$^+$.

Example 61

4-[6-(1-Cyclobutyl-piperidin-4-yloxy)-3-isopropyl-5-methyl-benzofuran-2-carbonyl]-piperazine-1-carboxylic acid methyl ester The title compound was prepared in analogy to example 58, but using in the final step piperazine-1-carboxylic acid methyl ester instead of 4,4-difluoropiperidine, as white foam.
MS (ISP): 498.3 [M+H]$^+$.

Example 62

4-[6-(1-Cyclobutyl-piperidin-4-yloxy)-3-phenyl-benzofuran-2-carbonyl]-piperazine-1-carboxylic acid methyl ester This compound was prepared in analogy to example 55, but using in the final step piperazine-1-carboxylic acid methyl ester instead of 4,4-difluoropiperidine, as white foam.
MS (ISP): 518.4 [M+H]$^+$.

Example 63

4-[6-(1-Cyclobutyl-piperidin-4-yloxy)-3-(4-fluoro-phenyl)-benzofuran-2-carbonyl]-piperazine-1-carboxylic acid methyl ester This compound was prepared in analogy to example 62, but using in the first step 3-(4-fluoro-phenyl)-6-hydroxy-benzofuran-2-carboxylic acid ethyl ester instead of 6-hydroxy-3-phenyl-benzofuran-2-carboxylic acid ethyl ester, as white foam.
MS (ISP): 536.3 [M+H]$^+$.

Example 64

[6-(1-Cyclobutyl-piperidin-4-yloxy)-3-(4-fluoro-phenyl)-benzofuran-2-yl]-((cis)-2,6-dimethyl-morpholin-4-yl)-methanone The compound was prepared in analogy to example 63, but using in the final step (cis)-2,6-dimethyl-morpholine instead of piperazine-1-carboxylic acid methyl ester, as off-white foam.
MS (ISP): 507.3 [M+H]$^+$.

Example 65

[6-(1-Cyclobutyl-piperidin-4-yloxy)-3-(4-fluoro-phenyl)-benzofuran-2-yl]-(4,4-difluoro-piperidin-1-yl)-methanone The compound was prepared in analogy to example 63, but using in the final step 4,4-difluoro-piperidine instead of piperazine-1-carboxylic acid methyl ester, as white foam.
MS (ISP): 513.3 [M+H]$^+$.

Example 66

(1,1-Dioxo-$_1\lambda$6thiomorpholin-4-yl)-[6-(1-isopropyl-piperidin-4-yloxy)-3-phenyl-benzofuran-2-yl]-methanone The compound was prepared in analogy to example 17, but using in the final step thiomorpholine 1,1-dioxide instead of 4,4-difluoropiperidine, as white solid.
MS (ISP): 497.1 [M+H]$^+$.

Example 67

[6-(1-Cyclobutyl-piperidin-4-yloxy)-3-(4-fluoro-phenyl)-benzofuran-2-yl]-(1,1-dioxo-$_1\lambda$6thiomorpholin-4-yl)-methanone This compound was prepared in analogy to example 63, but using in the final step thiomorpholine 1,1-dioxide instead of piperazine-1-carboxylic acid methyl ester, as white solid.
MS (ISP): 527.1 [M+H]$^+$.

Example 68

4-[6-Chloro-5-(1-isopropyl-piperidin-4-yloxy)-benzo[b]thiophene-2-carbonyl]-piperazine-1-carboxylic acid methyl ester Step 1: 6-Chloro-5-methoxy-benzo[b]thiophene-2-carboxylic acid methyl ester
To a solution of 4-chloro-2-fluoro-5-methoxybenzaldehyde (0.821 g, 4.35 mmol) in 8.7 mL of DMSO were successively added K₂CO₃ (1.81 g, 3 eq.) and methyl thioglycolate (0.474 mL, 1.2 eq.), and the mixture was vigorously stirred at 50° C. for 2 h. After cooling, the reaction mixture was poured onto crashed ice/HCl, twofold extracted with AcOEt, washed with water, dried over sodium sulfate, and evaporated. Flash chromatography (SiO₂, hexane/AcOEt=85/15), followed by crystallization from heptane/AcOEt, yielded 0.300 g of the title compound as off-white solid.

MS (EI): 256.1 [M]⁺.

The remaining steps were performed as alluded to in Example 9, step 2 and following, to give 4-[6-Chloro-5-(1-isopropyl-piperidin-4-yloxy)-benzo[b]thiophene-2-carbonyl]-piperazine-1-carboxylic acid methyl ester as white foam.

MS (ISP): 480.2 [M+H]⁺.

Example 69

[6-Chloro-5-(1-isopropyl-piperidin-4-yloxy)-benzo[b]thiophen-2-yl]-(1,1-dioxo-₁λ6thiomorpholin-4-yl)-methanone The title compound was prepared in analogy to example 68, but using in the final step thiomorpholine 1,1-dioxide instead of piperazine-1-carboxylic acid methyl ester, as white solid.

MS (ISP): 471.0 [M+H]⁺.

Example 70

[5-Chloro-3-isopropyl-6-(1-isopropyl-piperidin-4-yloxy)-benzofuran-2-yl]-((cis)-2,6-dimethyl morpholin-4-yl)-methanone This compound was prepared in analogy to Example 36, but using in the final step (cis)-2,6-dimethyl-morpholine instead of 4,4-difluoro-piperidine, as colorless gum.

MS (ISP): 477.3 [M+H]⁺.

Example 71

[5-Chloro-3-isopropyl-6-(1-isopropyl-piperidin-4-yloxy)-benzofuran-2-yl]-(1,1-dioxo-₁λ6thiomorpholin-4-yl)-methanone This compound was prepared in analogy to Example 36, but using in the final step thiomorpholine 1,1-dioxide instead of 4,4-difluoro-piperidine, as white crystals.

MS (ISP): 497.1 [M+H]⁺.

Example 72

4-[5-Chloro-3-isopropyl-6-(1-isopropyl-piperidin-4-yloxy)-benzofuran-2-carbonyl]-piperazine-1-carboxylic acid methyl ester This compound was prepared in analogy to Example 36, but using in the final step piperazine-1-carboxylic acid methyl ester instead of 4,4-difluoro-piperidine, as white crystals.

MS (ISP): 506.3 [M+H]⁺.

Example 73

[5-Chloro-6-(1-cyclobutyl-piperidin-4-yloxy)-3-isopropyl-benzofuran-2-yl]-(4,4-difluoro-piperidin-1-yl)-methanone The title compound was prepared in analogy to example 19, but using in the first step 5-chloro-6-hydroxy-3-isopropyl-benzofuran-2-carboxylic acid ethyl ester instead of 6-hydroxy-benzo[b]thiophene-2-carboxylic acid ethyl ester, as light brown gum.

MS (ISP): 495.3 [M+H]⁺.

Example 74

[5-Chloro-6-(1-cyclobutyl-piperidin-4-yloxy)-3-isopropyl-benzofuran-2-yl]-((cis)-2,6-dimethyl-morpholin-4-yl)-methanone This compound was prepared in analogy to Example 73, but using in the final step (cis)-2,6-dimethyl-morpholine instead of 4,4-difluoro-piperidine, as light brown gum.

MS (ISP): 489.2[M+H]⁺.

Example 75

[5-Chloro-6-(1-cyclobutyl-piperidin-4-yloxy)-3 isopropyl-benzofuran-2-yl]-(1,1-dioxo-₁λ6thiomorpholin-4-yl)-methanone This compound was prepared in analogy to Example 73, but using in the final step thiomorpholine 1,1-dioxide instead of 4,4-difluoro-piperidine, as white crystals.

MS (ISP): 509.4[M+H]⁺.

Example 76

4-[5-Chloro-6-(1-cyclobutyl-piperidin-4-yloxy)-3-isopropyl-benzofuran-2-carbonyl]-piperazine-1-carboxylic acid methyl ester The title compound was prepared in analogy to Example 73, but using in the final step piperazine-1-carboxylic acid methyl ester instead of 4,4-difluoro-piperidine, as light yellow gum.

MS (ISP): 518.3[M+H]⁺.

Example 77

[5-Chloro-6-(1-cyclobutyl-piperidin-4-yloxy)-3-phenyl-benzofuran-2-yl]-(1,1-dioxo-₁λ6thiomorpholin-4-yl)methanone The title compound was prepared in analogy to example 75, but using in the first step 5-chloro-6-hydroxy-3-phenyl-benzofuran-2-carboxylic acid ethyl ester instead of 5-chloro-6-hydroxy-3-isopropyl-benzofuran-2-carboxylic acid ethyl ester, as white crystals.

MS (ISP): 543.2 [M+H]⁺.

Example 78

4-[5-Chloro-6-(1-cyclobutyl-piperidin-4-yloxy)-3-phenyl-benzofuran-2-carbonyl]-piperazine-1-carboxylic acid methyl ester This compound was prepared in analogy to Example 77, but using in the final step piperazine-1-carboxylic acid methyl ester instead of thiomorpholine 1,1-dioxide, as white solid.

MS (ISP): 552.1[M+H]+.

Example 79

4-[5-Chloro-3-(4-fluoro-phenyl)-6-(1-isopropyl-piperidin 4-yloxy)-benzofuran-2-carbonyl]-piperazine-1-carboxylic acid methyl ester Step 1: (5-Chloro-2,4-Dimethoxy-phenyl)-(4-fluoro-phenyl)-methanone Chloro-2,4-Dimethoxy-benzene (5.00 g, 29.0 mmol) and $AlCl_3$ (4.63 g, 1.2 eq.) were dissolved in 290 ml of $CH_2Cl_2$ and cooled down to 0° C. 4-Fluoro-benzoyl chloride (3.47 mL, 1.0 eq.) was slowly added via dropping funnel and the mixture allowed to react for 2 additional h at ambient temperature. Pouring onto crashed ice, twofold extraction with AcOEt, washing with brine, drying over sodium sulfate, and evaporation of the solvents left 8.41 g of the title compound used crude for the next step.

Step 2: (5-Chloro-2-hydroxy-4-methoxy-phenyl)-(4-fluoro-phenyl)-methanone

The above prepared (5-chloro-2,4-Dimethoxy-phenyl)-(4-fluoro-phenyl)-methanone (8.41 g, 28.5 mmol) was dissolved in 115 mL of acetonitrile and treated successively with sodium iodide (6.51 g, 1.5 eq.) and $AlCl_3$ (3.86 g, 1.0 eq.), and the mixture kept at 80° C. for 0.75 h. Cooling, pouring onto crashed ice, twofold extraction with AcOEt, washing with brine, drying over sodium sulfate, and evaporation of the solvents, followed by a short flash chromatography ($SiO_2$, hexane/AcOEt=9/1), afforded 6.94 g of the title compound as light yellow solid.

MS (ISP): 279.3 [M–H]+.

Step 3: [4-Chloro-2-(4-fluoro-benzoyl)-5-methoxy-phenoxy]-acetic acid ethyl ester To a solution of the above prepared (5-chloro-2-hydroxy-4-methoxy-phenyl)-(4-fluoro-phenyl)-methanone (6.94 g, 24.7 mmol) in 50 mL acetonitrile were successively added $Cs_2CO_3$ (9.67 g, 1.2 eq.) and ethyl bromoacetate (3.01 mL, 1.1 eq.) and the mixture vigorously stirred at ambient temperature for 1 h. Pouring onto crashed ice/$NH_4Cl$, twofold extraction with AcOEt, washing with brine, drying over sodium sulfate, and evaporation of the solvents left 8.97 g of the title compound as off-white solid, used directly for the next step.

MS (ISP): 367.0 [M+H]+.

The remaining steps were performed as described in Example 49, step 6 and following, but using in the last step piperazine-1-carboxylic acid methyl ester instead of 4,4-difluoro-piperidine, to give 4-[5-Chloro-3-(4-fluoro-phenyl)-6-(1-isopropyl-piperidin-4-yloxy)-benzofuran-2-carbonyl]-piperazine-1-carboxylic acid methyl ester as white foam.

MS (ISP): 558.2 [M+H]+.

Example 80

[5-Chloro-3-(4-fluoro-phenyl)-6-(1-isopropyl-piperidin-4-yloxy)-benzofuran-2-yl]-((cis)-2,6-dimethyl-morpholin-4-yl)-methanone This compound was prepared in analogy to Example 79, but using in the final step (cis)-2,6-dimethyl-morpholine instead of piperazine-1-carboxylic acid methyl ester, as white foam.

MS (ISP): 529.2[M+H]+.

Example 81

[5-Chloro-3-(4-fluoro-phenyl)-6-(1-isopropyl-piperidin-4-yloxy)-benzofuran-2-yl]-(4,4-difluoro-piperidin-1-yl)-methanone The compound was prepared in analogy to Example 79, but using in the final step 4,4-difluoropiperidine instead of piperazine-1-carboxylic acid methyl ester, as white foam.

MS (ISP): 535.3[M+H]+.

Example 82

[5-Chloro-3-(4-fluoro-phenyl)-6-(1-isopropyl-piperidin-4-yloxy)-benzofuran-2-yl]-(1,1-dioxo-$_1\lambda$6thiomorpholin-4-yl)-methanone This compound was prepared in analogy to Example 79, but using in the final step thiomorpholine 1,1-dioxide instead of piperazine-1-carboxylic acid methyl ester, as white solid.

MS (ISP): 549.2[M+H]+.

Example 83

4-[5-Chloro-6-(1-cyclobutyl-piperidin-4-yloxy)-3-(4-fluoro-phenyl)-benzofuran-2-carbonyl]-piperazine-1-carboxylic acid methyl ester The compound was prepared as alluded to in Example 78, but using in the first step 5-chloro-3-(4-fluoro-phenyl)-6-hydroxy-benzofuran-2-carboxylic acid ethyl ester instead of 5-chloro-6-hydroxy-3-phenyl-benzofuran-2-carboxylic acid ethyl ester, as white foam.

MS (ISP): 570.4 [M+H]+.

Example 84

[5-Chloro-6-(1-cyclobutyl-piperidin-4-yloxy)-3-(4-fluoro-phenyl)-benzofuran-2-yl]-((cis)-2,6-dimethyl-morpholin-4-yl)-methanone The compound was prepared in analogy to Example 83, but using in the final step (cis)-2,6-dimethyl-morpholine instead of piperazine-1-carboxylic acid methyl ester, as off-white foam.

MS (ISP): 541.2[M+H]+.

Example 85

[5-Chloro-6-(1-cyclobutyl-piperidin-4-yloxy)-3-(4-fluoro-phenyl)-benzofuran-2-yl]-(1,1-dioxo-1λ6thiomorpholin-4-yl)-methanone The compound was prepared in analogy to Example 83, but using in the final step thiomorpholine 1,1-dioxide instead of piperazine-1-carboxylic acid methyl ester, as white solid.
MS (ISP): 561.3 [M+H]$^+$.

Example 86

[5-Chloro-6-(1-cyclobutyl-piperidin-4-yloxy)-3-(4-fluoro-phenyl)-benzofuran-2-yl]-(4,4-difluoro-piperidin-1-yl)-methanone This compound was prepared in analogy to Example 83, but using in the final step 4,4-difluoropiperidine instead of piperazine-1-carboxylic acid methyl ester, as white foam.
MS (ISP): 547.2 [M+H]$^+$.

Example 87

[5-Chloro-6-(1-isopropyl-piperidin-4-yloxy)-3-methyl-benzofuran-2-yl]-(4,4-difluoro-piperidin-1-yl)-methanone Step 1: 1-(5-Chloro-2-hydroxy-4-methoxy-phenyl)-ethanone Chloro-2,4-dimethoxybenzene (4.94 g, 28.6 mmol) and AlCl$_3$ (4.58 g, 1.2 eq.) were dissolved in 280 ml of CH$_2$Cl$_2$ and cooled down to 0° C. Acetyl chloride (2.03 mL, 1.0 eq.) was slowly added via syringe and the mixture allowed to react for another 3 h at ambient temperature. Pouring onto crashed ice, twofold extraction with AcOEt, washing with water and brine, drying over magnesium sulfate, and evaporation of the solvents, followed by short flash chromatography (SiO$_2$, hexane/AcOEt=95/5), yielded 4.22 g of the title compound as white crystals.
MS (ISP): 199.1 [M–H]$^-$.

Step 2: (2-Acetyl-4-chloro-5-methoxy-phenoxy)-acetic acid ethyl ester

To a solution of the above prepared 1-(5-chloro-2-hydroxy-4-methoxy-phenyl)-ethanone (4.22 g, 21.0 mmol) in 50 mL of acetonitrile were successively added Cs$_2$CO$_3$ (8.22 g, 1.2 eq.) and ethyl bromoacetate (2.44 mL, 1.05 eq.) and the mixture vigorously stirred at ambient temperature for 2 h. Pouring onto crashed ice/NH$_4$Cl, twofold extraction with AcOEt, washing with water, drying over magnesium sulfate, and evaporation of the solvents left 6.05 g of the title compound as off-white solid, used directly for the next step.
MS (ISP): 286.9 [M+H]$^+$.

Step 3: 5-Chloro-6-methoxy-3-methyl-benzofuran-2-carboxylic acid ethyl ester

The above prepared (2-acetyl-4-chloro-5-methoxy-phenoxy)-acetic acid ethyl ester-(6.05 g, 21.1 mmol) was dissolved in 45 mL of dimethoxyethane and treated at –15° C. with KOtBu (0.947 g, 0.4 eq.). After keeping for 45 Min. at –15° C. and 5 h at 0° C., the reaction mixture was poured onto crashed ice/HCl, twofold extracted with AcOEt, washed with water, dried over magnesium sulfate, and evaporated to dryness to leave 5.26 g of crude product. Flash chromatography (SiO$_2$, hexane/AcOEt=9/1) of the latter afforded 2.32 g of the title compound as white crystals.
MS (ISP): 269.0 [M+H]$^+$.

Step 4: 5-Chloro-6-hydroxy-3 methyl-benzofuran-2-carboxylic acid ethyl ester

The above prepared 5-chloro-6-methoxy-3-methyl-benzofuran-2-carboxylic acid ethyl ester (2.32 g, 8.63 mmol) was dissolved in 50 mL of CH$_2$Cl$_2$, cooled to 0° C., and treated with BBr$_3$ (17.3 mL of 1M solution in CH$_2$Cl$_2$, 2 eq.). After 5 h at 0° C., the reaction mixture was carefully poured onto crashed ice, twofold extracted with AcOEt, washed with water, dried over magnesium sulfate, and evaporated to dryness. Since substantial amount of free acid had been formed, the crude product was again esterified by treatment with anhydrous HCl in EtOH for 48 h at 48° C. Standard work-up and ensuing flash chromatography (SiO$_2$, hexane/AcOEt=8/2) yielded finally 1.607 g of the title compound as light yellow crystals.
MS (ISP): 255.0 [M+H]$^+$.

Step 5: 5-Chloro-6-(1-isopropyl-piperidin-4-yloxy)-3-methyl-benzofuran-2-carboxylic acid ethyl ester The above prepared 5-chloro-6-hydroxy-3-methyl-benzofuran-2-carboxylic acid ethyl ester (0.700 g, 2.75 mmol) was dissolved in 12 mL of THF and treated successively at –10° C. with 1-isopropyl-piperidin-4-ol (0.551 g, 1.4 eq.), triphenylphosphine (1.001 g, 1.4 eq.) and DIAD (0.755 mL, 1.4 eq.), and the mixture then kept at ambient temperature for another 4 h. Pouring onto crashed ice/NH$_4$Cl, twofold extraction with AcOEt, washing with water and brine, drying over magnesium sulfate, and evaporation of the solvents, followed by flash chromatography (SiO$_2$, NEt$_3$/AcOEt=2/98), produced 0.990 g of the title compound as light yellow gum.
MS (ISP): 380.3 [M+H]$^+$.

Step 6: 5-Chloro-6-(1-isopropyl-piperidin-4-yloxy)-3-methyl-benzofuran-2-carboxylic acid The above prepared 5-chloro-6-(1-isopropyl-piperidin-4-yloxy)-3-methyl-benzofuran-2-carboxylic acid ethyl ester (0.897 g, 2.36 mmol) was dissolved in 4.8 mL of THF/ethanol=1/1 and treated with 1.18 mL of aq. NaOH (3M, 1.5 eq.). The mixture was stirred for 3 h at ambient temperature and was then neutralized by adding 1.77 mL of 2M HCl (1.5 eq.). Careful evaporation of all solvents and drying afforded finally 1.161 g of the title compound as off-white solid, contaminated with innocuous inorganic salts.
MS (ISP): 350.3 [M–H]$^-$.

Step 7: [5-Chloro-6-(1-isopropyl-piperidin-4-yloxy)-3-methyl-benzofuran-2-yl]-(4,4-difluoro-piperidin-1-yl)-methanone In a flask were mixed together the above prepared 5-chloro-6-(1-isopropyl-piperidin-4-yloxy)-3-methyl-benzofuran-2-carboxylic acid (0.200 g, 0.406 mmol, corrected for purity), 4,4-difluoropiperidine hydrochloride (0.077 g, 1.2 eq.), (benzotriazol-1-yloxy)-tris-(dimethylamino)phosphonium hexafluorophosphate (0.216 g, 1.2 eq.) and 2.4 eq. of N-ethyldiisopropylamine (0.166 mL) in 4 mL of abs. THF and stirred over night at ambient temperature. Pouring onto crashed ice/AcOEt/NH$_4$Cl-solution, twofold extraction with AcOEt, washing with water and brine, drying over magnesium sulfate, and evaporation of the solvents, followed by flash chromatography (SiO$_2$, NEt$_3$/AcOEt=2/98) yielded 0.183 g of the title compound as white solid.

MS (ISP): 455.4 [M+H]$^+$.

Example 88

[5-Chloro-6-(1-isopropyl-piperidin-4-yloxy)-3-methyl-benzofuran-2-yl]-((cis)-2,6-dimethyl-morpholin-4-yl)-methanone This compound was prepared in analogy to example 87, but using in the final step (cis)-2,6-dimethyl-morpholine instead of 4,4-difluoropiperidine, as white foam.

MS (ISP): 449.2 [M+H]$^+$.

Example 89

[5-Chloro-6-(1-isopropyl-piperidin-4-yloxy)-3-methyl-benzofuran-2-yl]-(1,1-dioxo-$_1$λ6-thiomorpholin-4-yl)-methanone This compound was prepared in analogy to example 87, but using in the final step thiomorpholine 1,1-dioxide instead of 4,4-difluoropiperidine, as white crystals.

MS (ISP): 469.2 [M+H]$^+$.

Example 90

4-[5-Chloro-6-(1-isopropyl-piperidin-4-yloxy)-3-methyl-benzofuran-2-carbonyl]-piperazine-1-carboxylic acid methyl ester This compound was prepared in analogy to example 87, but using in the final step piperazine-1-carboxylic acid methyl ester instead of 4,4-difluoropiperidine, as white foam.

MS (ISP): 478.5 [M+H]$^+$.

Example 91

[5-Chloro-6-(1-cyclobutyl-piperidin-4-yloxy)-3-methyl-benzofuran-2-yl]-(4,4-difluoro-piperidin-1-yl)-methanone This compound was prepared in analogy to example 87 as white foam.

MS (ISP): 467.3 [M+H]$^+$.

However, instead of step 5, the following reaction sequence A-C was applied:

Step A: 4-(5-Chloro-2-ethoxycarbonyl-3-methyl-benzofuran-6-yloxy)-piperidine-1-carboxylic acid tert-butyl ester The above prepared 5-chloro-6-hydroxy-3-methyl-benzofuran-2-carboxylic acid ethyl ester (0.900 g, 3.53 mmol) was dissolved in 15 mL of THF and treated successively at −10° C. with 4-hydroxy-piperidine-1-carboxylic acid tert-butyl ester (0.996 g, 1.4 eq.), triphenylphosphine (1.298 g, 1.4 eq.) and DIAD (0.971 mL, 1.4 eq.), and the mixture then kept at ambient temperature for another 3 h. Pouring onto crashed ice/NH$_4$Cl, twofold extraction with AcOEt, washing with water and brine, drying over magnesium sulfate, and evaporation of the solvents, followed by flash chromatography (SiO$_2$, hexane/AcOEt=85/15), gave 1.459 g of the title compound as colorless gum.

MS (ISP): 438.3 [M+H]$^+$, 382.5 [M+H−tBu]$^+$, 338.3 [M+H−BOC]$^+$.

Step B: 5-Chloro-3-methyl-6-(piperidin-4-yloxy)-benzofuran-2-carboxylic acid ethyl ester The above prepared 4-(5-chloro-2-ethoxycarbonyl-3-methyl-benzofuran-6-yloxy)-piperidine-1-carboxylic acid tert-butyl ester (1.457 g, 3.327 mmol) was dissolved in 8 mL of dioxane and treated with HCl (16.5 mL of 4N [dioxane], 20 eq.) and the mixture kept at ambient temperature for 2 h. Careful evaporation of all solvents and drying yielded 1.36 of the title product as hydrochloride as white crystals, which was further processed without additional purification.

MS (ISP): 338.3 [M+H]$^+$.

Step C: 5-Chloro-6-(1-cyclobutyl-piperidin-4-yloxy)-3-methyl-benzofuran-2-carboxylic acid ethyl ester The above prepared 5-chloro-3-methyl-6-(piperidin-4-yloxy)-benzofuran-2-carboxylic acid ethyl ester (1.35 g, 3.32 mmol) was dissolved in 45 mL of CH$_2$Cl$_2$ and treated successively with cyclobutanone (0.506 g, 2 eq.), acetic acid (0.413 mL, 2 eq.) and sodium triacetoxyborohydride (1.529 g, 2 eq.), and the mixture then kept at ambient temperature for 5 h. Pouring onto crashed ice/NaHCO$_3$, five fold extraction with AcOEt, washing with water and brine, drying over magnesium sulfate, and evaporation of the solvents, followed by followed by flash chromatography (SiO$_2$, NEt$_3$/AcOEt=2/98) generated 1.190 g of the title compound as white crystals.

MS (ISP): 392.1 [M+H]$^+$.

Example 92

[5-Chloro-6-(1-cyclobutyl-piperidin-4-yloxy)-3-methyl-benzofuran-2-yl]-((cis)-2,6-dimethyl-morpholin-4-yl)-methanone This compound was prepared in analogy to example 91, but using in the final step (cis)-2,6-dimethyl-morpholine instead of 4,4-difluoropiperidine, as white solid.

MS (ISP): 461.3 [M+H]$^+$.

Example 93

[5-Chloro-6-(1-cyclobutyl-piperidin-4-yloxy)-3-methyl-benzofuran-2-yl]-(1,1-dioxo-$_1$λ6-thiomorpholin-4-yl)-methanone This compound was prepared in analogy to example 91, but using in the final step thiomorpholine 1,1-dioxide instead of 4,4-difluoropiperidine, as white crystals.

MS (ISP): 481.23 [M+H]$^+$.

Example 94

4-[5-Chloro-6-(1-cyclobutyl-piperidin-4-yloxy)-3-methyl-benzofuran-2-carbonyl]-piperazine-1-carboxylic acid methyl ester This compound was prepared in analogy to example 91, but using in the final step piperazine-1-carboxylic acid methyl ester instead of 4,4-difluoropiperidine, as white foam.

MS (ISP): 490.4 [M+H]$^+$.

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

What is claimed:

1. A compound of the formula

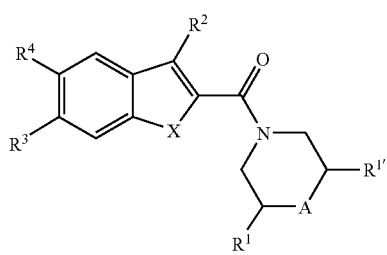

wherein

X is S or O;

A is selected from the group consisting of O, $CF_2$, $S(O)_2$, N—$R^5$ wherein $R^5$ is lower alkyl, NCO—$R^6$ wherein $R^6$ is lower alkyl and NCOO—$R^7$ wherein $R^7$ is lower alkyl;

$R^1$ and $R^{1'}$ independently from each other are hydrogen or lower alkyl;

$R^2$ is selected from the group consisting of hydrogen,
lower alkyl, cycloalkyl, lower cycloalkylalkyl,
lower hydroxyalkyl, lower alkoxyalkyl,
phenyl unsubstituted or substituted with one to three groups independently selected from lower alkyl, halogen, cyano, morpholinyl, lower alkoxy, lower alkoxycarbonyl, lower halogenalkyl, lower halogenalkoxy, lower hydroxyalkyl, lower alkylsulfonyl or lower alkylsulfonylamino,
lower phenylalkyl, wherein the phenyl ring may be unsubstituted or substituted with one to three groups independently selected from lower alkyl, halogen, cyano, morpholinyl, lower alkoxy, lower alkoxycarbonyl, lower halogenalkyl, lower halogenalkoxy, lower hydroxyalkyl, lower alkylsulfonyl or lower alkylsulfonylamino, and
heteroaryl unsubstituted or substituted with one or two groups independently selected from lower alkyl, lower alkoxy, cyano, morpholinyl or halogen;
one of $R^3$ or $R^4$ is selected from the group consisting of hydrogen, halogen, lower alkoxy and lower alkyl; and
the other one of $R^3$ and $R^4$ is a group G selected from

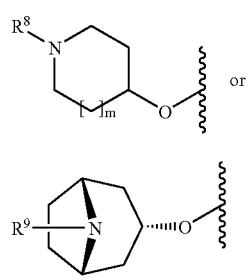

wherein
m is 0 or 1;
$R^8$ is selected from the group consisting of lower alkyl, cycloalkyl, lower halogenalkyl and lower alkoxycarbonyl;
$R^9$ is selected from the group consisting of lower alkyl, cycloalkyl, lower halogenalkyl and lower alkoxycarbonyl;
or a pharmaceutically acceptable salt thereof.

2. The compound of claim 1, wherein X is O.
3. The compound of claim 1, wherein X is S.
4. The compound of claim 1 wherein A is S(O)$_2$.
5. The compound of claim 1, wherein A is selected from the group consisting of N—$R^5$ wherein $R^5$ is lower alkyl, NCO—$R^6$ wherein $R^6$ is lower alkyl and NCOO—$R^7$ wherein $R^7$ is lower alkyl.
6. The compound of claim 5, wherein A is NCOO—$R^7$ wherein $R^7$ is lower alkyl.
7. The compound of claim 1, wherein A is CF$_2$.
8. The compound of claim 1, wherein $R^1$ and $R^{1'}$ are hydrogen.
9. The compound of claim 1, wherein A is O.
10. The compound of claim 9, wherein $R^1$ and $R^{1'}$ are methyl.
11. The compound of claim 10, wherein $R^2$ is selected from the group consisting of hydrogen, lower alkyl, and phenyl unsubstituted or substituted with one to three groups independently selected from lower alkyl, halogen, cyano, morpholinyl, lower alkoxy, lower alkoxycarbonyl, lower halogenalkyl, lower halogenalkoxy, lower hydroxyalkyl, lower alkylsulfonyl or lower alkylsulfonylamino.

12. The compound of claim 11, wherein
one of $R^3$ or $R^4$ is selected from the group consisting of hydrogen, halogen and lower alkyl; and the other one of $R^3$ and $R^4$ is a group G selected from

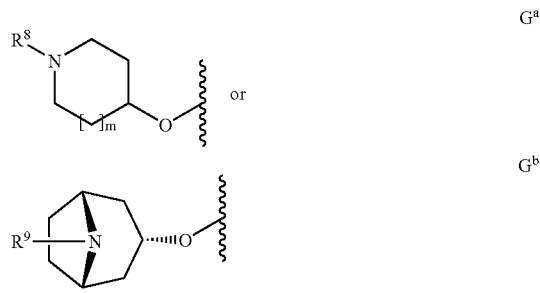

wherein
m is 0 or 1;
$R^8$ is selected from the group consisting of lower alkyl, cycloalkyl, lower halogenalkyl and lower alkoxycarbonyl;
$R^9$ is selected from the group consisting of lower alkyl, cycloalkyl, lower halogenalkyl and lower alkoxycarbonyl.

13. The compound of claim 12, wherein
one of $R^3$ or $R^4$ is selected from the group consisting of hydrogen, halogen and lower alkyl; and the other one of $R^3$ and $R^4$ is the group $G^a$

wherein m is 0 or 1; and $R^8$ is selected from the group consisting of lower alkyl, cycloalkyl, lower halogenalkyl and lower alkoxycarbonyl.

14. The compound of claim 12, wherein
one of $R^3$ or $R^4$ is hydrogen and the other one of $R^3$ and $R^4$ is

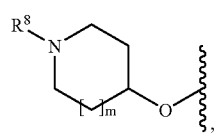

wherein m is 0 or 1; and $R^8$ is selected from the group consisting of lower alkyl, cycloalkyl, lower halogenalkyl and lower alkoxycarbonyl.

15. The compound of claim 14, wherein $R^8$ is lower alkyl or cycloalkyl.
16. The compound of claim 15, wherein $R^8$ is isopropyl or cyclobutyl.

17. The compound of claim 16, wherein m is 1.

18. A compound of claim 1, selected from the group consisting of
[5-(1-cyclobutyl-piperidin-yloxy)-benzofuran-2-yl]-(4,4-difluoro-piperidin-1-yl)-methanone,
4-[3-(4-fluoro-phenyl)-6-(1-isopropyl-piperidin-4-yloxy)-benzofuran-2-carbonyl]-piperazine-1-carboxylic acid methyl ester,
4-[6-(1-cyclobutyl-piperidin-4-yloxy)-3-phenyl-benzofuran-2-carbonyl]-piperazine-1-carboxylic acid methyl ester,
4-[6-(1-cyclobutyl-piperidin-4-yloxy)-3-(4-fluoro-phenyl)-benzofuran-2-carbonyl]-piperazine-1-carboxylic acid methyl ester,
[6-(1-cyclobutyl-piperidin-4-yloxy)-3-(4-fluoro-phenyl)-benzofuran-2-yl]-((cis)-2,6-dimethyl-morpholin-4-yl)-methanone,
[6-(1-cyclobutyl-piperidin-4-yloxy)-3-(4-fluoro-phenyl)-benzofuran-2-yl]-(4,4-difluoro-piperidin-1-yl)-methanone,
[6-(1-cyclobutyl-piperidin-4-yloxy)-3-(4-fluoro-phenyl)-benzofuran-2-yl]-(1,1-dioxo-$_1\lambda$6-thiomorpholin-4-yl)-methanone,
4-[5-chloro-6-(1-cyclobutyl-piperidin-4-yloxy)-3-phenyl-benzofuran-2-carbonyl]-piperazine-1-carboxylic acid methyl ester,
4-[5-chloro-3-(4-fluoro-phenyl)-6-(1-isopropyl-piperidin-4-yloxy)-benzofuran-2-carbonyl]-piperazine-1-carboxylic acid methyl ester,
[5-chloro-3-(4-fluoro-phenyl)-6-(1-isopropyl-piperidin-4-yloxy)-benzofuran-2-yl]-(1,1-dioxo-$_1\lambda$6-thiomorpholin-4-yl)-methanone,
4-[5-chloro-6-(1-cyclobutyl-piperidin-4-yloxy)-3-(4-fluoro-phenyl)-benzofuran-2-carbonyl]-piperazine-1-carboxylic acid methyl ester and
[5-chloro-6-(1-cyclobutyl-piperidin-4-yloxy)-3-(4-fluoro-phenyl)-benzofuran-2-yl]-(1,1-dioxo-$_1\lambda$6-thiomorpholin-4-yl)-methanone,
or a pharmaceutically acceptable salt thereof.

19. A process for the manufacture of compounds of claim 1, which process comprises
reacting a compound of the formula II

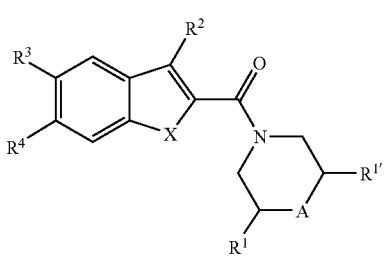

wherein X, A, $R^1$, $R^{1'}$ and $R^2$ are as defined in claim 1, one of $R^3$ or $R^4$ is selected from the group consisting of hydrogen, halogen and lower alkyl, and the other one of $R^3$ and $R^4$ is hydroxy, with an alcohol of the formula III

G-H  III wherein G is a group $G^a$ or $G^b$ as defined in claim 1, in the presence of a trialkylphosphine or triphenylphosphine and of an azo compound to obtain a compound of the formula I

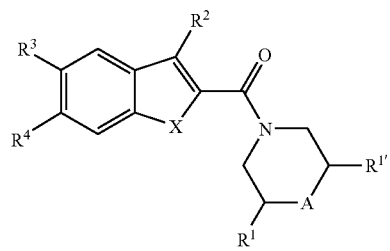

and, if desired, converting the compound obtained into a pharmaceutically acceptable salt.

20. A pharmaceutical composition comprising a compound of the formula

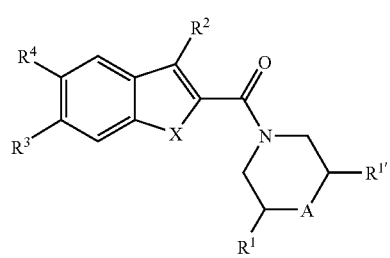

wherein

X is S or O;

A is selected from the group consisting of O, $CF_2$, S(O), N—$R^5$ wherein $R^5$ is lower alkyl, NCO—$R^6$ wherein $R^6$ is lower alkyl and NCOO—$R^7$ wherein $R^7$ is lower alkyl;

$R^1$ and $R^{1'}$ independently from each other are hydrogen or lower alkyl;

$R^2$ is selected from the group consisting of hydrogen,
lower alkyl, cycloalkyl, lower cycloalkylalkyl,
lower hydroxyalkyl, lower alkoxyalkyl,
phenyl unsubstituted or substituted with one to three groups independently selected from lower alkyl, halogen, cyano, morpholinyl, lower alkoxy, lower alkoxycarbonyl, lower halogenalkyl, lower halogenalkoxy, lower hydroxyalkyl, lower alkylsulfonyl or and lower alkylsulfonylamino,
lower phenylalkyl, wherein the phenyl ring may be unsubstituted or substituted with one to three groups independently selected from lower alkyl, halogen, cyano, morpholinyl, lower alkoxy, lower alkoxycarbonyl, lower halogenalkyl, lower halogenalkoxy, lower hydroxyalkyl, lower alkylsulfonyl or and lower alkylsulfonylamino, and
heteroaryl unsubstituted or substituted with one or two groups independently selected from lower alkyl, lower alkoxy, cyano, morpholinyl or and halogen;

one of $R^3$ or $R^4$ is selected from the group consisting of hydrogen, halogen, lower alkoxy and lower alkyl; and the other one of $R^3$ and $R^4$ is a group G selected from

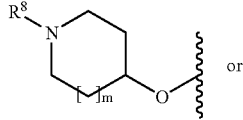
$G^a$ or

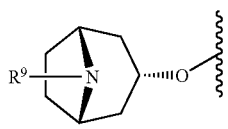
$G^b$ wherein m is 0 or 1;

$R^8$ is selected from the group consisting of lower alkyl, cycloalkyl, lower halogenalkyl and lower alkoxycarbonyl;

$R^9$ is selected from the group consisting of lower alkyl, cycloalkyl, lower halogenalkyl and lower alkoxycarbonyl;

or a pharmaceutically acceptable salts thereof together with a pharmaceutically acceptable carrier and/or adjuvant.

* * * * *

UNITED STATES PATENT AND TRADEMARK OFFICE
CERTIFICATE OF CORRECTION

| | | |
|---|---|---|
| PATENT NO. | : 7,534,788 B2 | Page 1 of 1 |
| APPLICATION NO. | : 12/173888 | |
| DATED | : May 19, 2009 | |
| INVENTOR(S) | : Peter Mohr et al. | |

It is certified that error appears in the above-identified patent and that said Letters Patent is hereby corrected as shown below:

In Claim 20 at Column 70, Line 40, please delete – "S(O)" and
Insert --S(O)2--

Signed and Sealed this

Fourteenth Day of July, 2009

JOHN DOLL
*Acting Director of the United States Patent and Trademark Office*